(12) United States Patent
Morgan et al.

(10) Patent No.: US 7,910,743 B2
(45) Date of Patent: *Mar. 22, 2011

(54) COMPOUNDS, COMPOSITIONS AND METHODS

(75) Inventors: Bradley P. Morgan, Moraga, CA (US); Alex Muci, San Francisco, CA (US); Erica Kraynack, Belmont, CA (US); Pu-Ping Lu, Foster City, CA (US); Todd Tochimoto, Foster City, CA (US); David J. Morgans, Jr., Los Altos, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/469,603

(22) Filed: May 20, 2009

(65) Prior Publication Data

US 2009/0324511 A1    Dec. 31, 2009

Related U.S. Application Data

(62) Division of application No. 11/498,986, filed on Aug. 4, 2006, now Pat. No. 7,538,223.

(60) Provisional application No. 60/705,848, filed on Aug. 4, 2005, provisional application No. 60/751,123, filed on Dec. 16, 2005.

(51) Int. Cl.
*C07D 211/68* (2006.01)
*C07D 401/04* (2006.01)
*C07D 401/14* (2006.01)

(52) U.S. Cl. .................................. 546/268.7; 546/274.1

(58) Field of Classification Search ................ 546/268.7
See application file for complete search history.

(56) References Cited

U.S. PATENT DOCUMENTS

| | | | | |
|---|---|---|---|---|
| 7,399,866 B2 * | 7/2008 | Morgan et al. | ................ | 546/194 |
| 7,491,826 B2 * | 2/2009 | Morgan et al. | ................ | 546/194 |
| 7,538,223 B2 * | 5/2009 | Morgan et al. | ................ | 546/194 |

* cited by examiner

*Primary Examiner* — Nizal S Chandrakumar
(74) *Attorney, Agent, or Firm* — Finnegan, Henderson, Farabow, Garrett & Dunner, LLP

(57) ABSTRACT

Certain substituted urea derivatives selectively modulate the cardiac sarcomere, for example by potentiating cardiac myosin, and are useful in the treatment of systolic heart failure including congestive heart failure.

8 Claims, No Drawings

COMPOUNDS, COMPOSITIONS AND METHODS

This application is a divisional of U.S. patent application Ser. No. 11/498,986, filed Aug. 4, 2006, now U.S. Pat. No. 7,538,223 which claims the benefit of U.S. Patent Application No. 60/705,848, filed Aug. 4, 2005 and of U.S. Patent Application No. 60/751,123, filed Dec. 16, 2005, each of which is hereby incorporated by reference.

The invention relates to substituted urea derivatives, particularly to compounds that selectively modulate the cardiac sarcomere, and specifically to compounds, pharmaceutical formulations and methods of treatment for systolic heart failure, including congestive heart failure.

The "sarcomere" is an elegantly organized cellular structure found in cardiac and skeletal muscle made up of interdigitating thin and thick filaments; it comprises nearly 60% of cardiac cell volume. The thick filaments are composed of "myosin," the protein responsible for transducing chemical energy (ATP hydrolysis) into force and directed movement. Myosin and its functionally related cousins are called motor proteins. The thin filaments are composed of a complex of proteins. One of these proteins, "actin" (a filamentous polymer) is the substrate upon which myosin pulls during force generation. Bound to actin are a set of regulatory proteins, the "troponin complex" and "tropomyosin," which make the actin-myosin interaction dependent on changes in intracellular $Ca^{2+}$ levels. With each heartbeat, $Ca^{2+}$ levels rise and fall, initiating cardiac muscle contraction and then cardiac muscle relaxation. Each of the components of the sarcomere contributes to its contractile response.

Myosin is the most extensively studied of all the motor proteins. Of the thirteen distinct classes of myosin in human cells, the myosin-II class is responsible for contraction of skeletal, cardiac, and smooth muscle. This class of myosin is significantly different in amino acid composition and in overall structure from myosin in the other twelve distinct classes. Myosin-II consists of two globular head domains linked together by a long alpha-helical coiled-coiled tail that assembles with other myosin-IIs to form the core of the sarcomere's thick filament. The globular heads have a catalytic domain where the actin binding and ATP functions of myosin take place. Once bound to an actin filament, the release of phosphate (cf. ATP to ADP) leads to a change in structural conformation of the catalytic domain that in turn alters the orientation of the light-chain binding lever arm domain that extends from the globular head; this movement is termed the powerstroke. This change in orientation of the myosin head in relationship to actin causes the thick filament of which it is a part to move with respect to the thin actin filament to which it is bound. Un-binding of the globular head from the actin filament (also $Ca^{2+}$ modulated) coupled with return of the catalytic domain and light chain to their starting conformation/orientation completes the contraction and relaxation cycle.

Mammalian heart muscle consists of two forms of cardiac myosin, alpha and beta, and they are well characterized. The beta form is the predominant form (>90 percent) in adult human cardiac muscle. Both have been observed to be regulated in human heart failure conditions at both transcriptional and translational levels, with the alpha form being down-regulated in heart failure.

The sequences of all of the human skeletal, cardiac, and smooth muscle myosins have been determined. While the cardiac alpha and beta myosins are very similar (93% identity), they are both considerably different from human smooth muscle (42% identity) and more closely related to skeletal myosins (80% identity). Conveniently, cardiac muscle myosins are incredibly conserved across mammalian species. For example, both alpha and beta cardiac myosins are >96% conserved between humans and rats, and the available 250-residue sequence of porcine cardiac beta myosin is 100% conserved with the corresponding human cardiac beta myosin sequence. Such sequence conservation contributes to the predictability of studying myosin based therapeutics in animal based models of heart failure.

The components of the cardiac sarcomere present targets for the treatment of heart failure, for example by increasing contractility or facilitating complete relaxation to modulate systolic and diastolic function, respectively.

Congestive heart failure ("CHF") is not a specific disease, but rather a constellation of signs and symptoms, all of which are caused by an inability of the heart to adequately respond to exertion by increasing cardiac output. The dominant pathophysiology associated with CHF is systolic dysfunction, an impairment of cardiac contractility (with a consequent reduction in the amount of blood ejected with each heartbeat). Systolic dysfunction with compensatory dilation of the ventricular cavities results in the most common form of heart failure, "dilated cardiomyopathy," which is often considered to be one in the same as CHF. The counterpoint to systolic dysfunction is diastolic dysfunction, an impairment of the ability to fill the ventricles with blood, which can also result in heart failure even with preserved left ventricular function. Congestive heart failure is ultimately associated with improper function of the cardiac myocyte itself, involving a decrease in its ability to contract and relax.

Many of the same underlying conditions can give rise to systolic and/or diastolic dysfunction, such as atherosclerosis, hypertension, viral infection, valvular dysfunction, and genetic disorders. Patients with these conditions typically present with the same classical symptoms: shortness of breath, edema and overwhelming fatigue. In approximately half of the patients with dilated cardiomyopathy, the cause of their heart dysfunction is ischemic heart disease due to coronary atherosclerosis. These patients have had either a single myocardial infarction or multiple myocardial infarctions; here, the consequent scarring and remodeling results in the development of a dilated and hypocontractile heart. At times the causative agent cannot be identified, so the disease is referred to as "idiopathic dilated cardiomyopathy." Irrespective of ischemic or other origin, patients with dilated cardiomyopathy share an abysmal prognosis, excessive morbidity and high mortality.

The prevalence of CHF has grown to epidemic proportions as the population ages and as cardiologists have become more successful at reducing mortality from ischemic heart disease, the most common prelude to CHF. Roughly 4.6 million people in the United States have been diagnosed with CHF; the incidence of such diagnosis is approaching 10 per 1000 after 65 years of age. Hospitalization for CHF is usually the result of inadequate outpatient therapy. Hospital discharges for CHF rose from 377,000 (in 1979) to 970,000 (in 2002) making CHF the most common discharge diagnosis in people age 65 and over. The five-year mortality from CHF approaches 50%. Hence, while therapies for heart disease have greatly improved and life expectancies have extended over the last several years, new and better therapies continue to be sought, for example, for CHF.

"Acute" congestive heart failure (also known as acute "decompensated" heart failure) involves a precipitous drop in cardiac function resulting from a variety of causes. For example in a patient who already has congestive heart failure, a new myocardial infarction, discontinuation of medications, and dietary indiscretions may all lead to accumulation of edema fluid and metabolic insufficiency even in the resting state. A therapeutic agent that increases cardiac function during such an acute episode could assist in relieving this metabolic insufficiency and speeding the removal of edema, facilitating the return to the more stable "compensated" congestive heart failure state. Patients with very advanced congestive heart failure particularly those at the end stage of the disease also could benefit from a therapeutic agent that increases cardiac function, for example, for stabilization while waiting for a heart transplant. Other potential benefits could be provided to patients coming off a bypass pump, for example, by administration of an agent that assists the stopped or slowed heart in resuming normal function. Patients who have diastolic dysfunction (insufficient relaxation of the heart muscle) could benefit from a therapeutic agent that modulates relaxation.

Inotropes are drugs that increase the contractile ability of the heart. As a group, all current inotropes have failed to meet the gold standard for heart failure therapy, i.e., to prolong patient survival. In addition, current agents are poorly selective for cardiac tissue, in part leading to recognized adverse effects that limit their use. Despite this fact, intravenous inotropes continue to be widely used in acute heart failure (e.g., to allow for reinstitution of oral medications or to bridge patients to heart transplantation) whereas in chronic heart failure, orally given digoxin is used as an inotrope to relieve patient symptoms, improve the quality of life, and reduce hospital admissions.

Given the limitations of current agents, new approaches are needed to improve cardiac function in congestive heart failure. The most recently approved short-term intravenous agent, milrinone, is now nearly fifteen years old. The only available oral drug, digoxin, is over 200 hundred years old. There remains a great need for agents that exploit new mechanisms of action and may have better outcomes in terms of relief of symptoms, safety, and patient mortality, both short-term and long-term. New agents with an improved therapeutic index over current agents will provide a means to achieve these clinical outcomes.

Current inotropic therapies improve contractility by increasing the calcium transient via the adenylyl cyclase pathway, or by delaying cAMP degradation through inhibition of phosphodiesterase (PDE), which can be detrimental to patients with heart failure.

Given the limitations of current agents, new approaches are needed to improve cardiac function in congestive heart failure. The most recently approved short-term intravenous agent, milrinone, is more than fifteen years old. The only available oral drug, digoxin, is over 200 hundred years old. There remains a great need for agents that exploit new mechanisms of action and may have better outcomes in terms of relief of symptoms, safety, and patient mortality, both short-term and long-term. New agents with an improved therapeutic index over current agents will provide a means to achieve these clinical outcomes.

The selectivity of agents directed at the cardiac sarcomere (for example, by targeting cardiac beta myosin) has been identified as an important means to achieve this improved therapeutic index. The present invention provides such agents (particularly sarcomere activating agents) and methods for their identification and use.

Another approach may be to directly activate cardiac myosin without changing the calcium transient to improving cardiac contractility. The present invention provides such agents (particularly myosin activating agents) and methods for their identification and use.

The present invention provides compounds, pharmaceutical compositions and methods for the treatment of heart failure including CHF, particularly systolic heart failure. The compositions are selective modulators of the cardiac sarcomere, for example, potentiating cardiac myosin.

Provided is at least one chemical entity chosen from compounds of Formula I

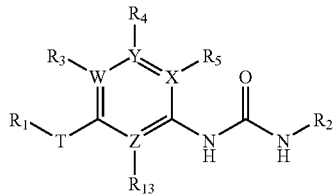

Formula I and pharmaceutically acceptable salts, solvates, chelates, non-covalent complexes, prodrugs, and mixtures thereof, wherein T is selected from —O—, —O-(optionally substituted lower alkylene)-, -(optionally substituted lower alkylene)-O—, —S—, —S-(optionally substituted lower alkylene)-, -(optionally substituted lower alkylene)-S—, —$SO_2$—, —$SO_2$-(optionally substituted lower alkylene)-, and -(optionally substituted lower alkylene)-$SO_2$—;

W, X, Y, and Z are independently selected from —C═ and —N═, provided that no more than two of W, X, Y, and Z are —N═;

$R_1$ is selected from optionally substituted alkyl, optionally substituted amino, optionally substituted aryl, optionally substituted heteroaryl, and optionally substituted heterocycloalkyl;

$R_2$ is selected from optionally substituted aryl, optionally substituted aralkyl; optionally substituted cycloalkyl, optionally substituted heteroaryl, optionally substituted heteroaralkyl and optionally substituted heterocycloalkyl;

$R_3$ is selected from hydrogen, halo, cyano, nitro, optionally substituted alkyl, optionally substituted heterocycloalkyl, and optionally substituted heteroaryl when W is —C═, and $R_3$ is absent when W is —N═;

$R_4$ is selected from hydrogen, halo, cyano, nitro, optionally substituted alkyl, optionally substituted heterocycloalkyl, and optionally substituted heteroaryl when Y is —C═, and $R_4$ is absent when Y is —N═; and $R_5$ is selected from hydrogen, halo, cyano, nitro, optionally substituted alkyl, optionally substituted heterocycloalkyl, and optionally substituted heteroaryl when X is —C═, and $R_5$ is absent when X is —N═;

$R_6$ and $R_7$ are independently selected from hydrogen, optionally substituted alkyl, optionally substituted cycloalkyl, optionally substituted heteroalkyl, optionally substituted heterocycloalkyl, optionally substituted aryl and optionally substituted heteroaryl;

$R_{13}$ is selected from hydrogen, halo, cyano, nitro, hydroxyl, optionally substituted alkyl, optionally substituted heterocycloalkyl, and optionally substituted heteroaryl when Z is —C═, and $R_{13}$ is absent when Z is —N═; and;

provided that:

if $R_3$ is hydrogen, halo or optionally substituted heteroaryl, then one of $R_{13}$ and $R_5$ is other than hydrogen, or W or X is —N═, or two of W, X, Y, and Z are —N═, or $R_1$ is optionally substituted alkyl or optionally substituted heterocycloalkyl comprising an optionally substituted sulfuric diamide subunit;

if R$_4$ is hydrogen, halo, nitro or optionally substituted heteroaryl, then one of R$_{13}$ and R$_5$ is other than hydrogen, or W or X is —N=, or two of W, X, Y, and Z are —N=, or R$_1$ is optionally substituted alkyl or optionally substituted heterocycloalkyl comprising an optionally substituted sulfuric diamide subunit; or if W, X, Y, and Z are —C=, or if X and W are both —C= and one of Y and Z is —N=, then one of R$_{13}$ and R$_5$ is other than hydrogen, or R$_3$ is not hydrogen, halo or optionally substituted heteroaryl, or R$_4$ is not hydrogen, halo, nitro or optionally substituted heteroaryl, or R$_1$ is optionally substituted alkyl or optionally substituted heterocycloalkyl comprising an optionally substituted sulfuric diamide subunit;

and further provided that if R$_1$ is amino or if R$_1$ is heteroaryl or heterocycloalkyl with a heteroatom bonded to T, then T is not —O—, —S—, —O-alkyl, or —S-alkyl.

Also provided is a pharmaceutical composition comprising a pharmaceutically acceptable excipient or adjuvant and at least one chemical entity as described herein for Formula I.

Also provided is a packaged pharmaceutical composition, comprising a pharmaceutical composition as described herein and instructions for using the composition to treat a patient suffering from a heart disease.

Also provided is a method of treating heart disease in a mammal which method comprises administering to a mammal in need thereof a therapeutically effective amount of at least one chemical entity as described herein for Formula I.

Also provided is a method for modulating the cardiac sarcomere in a mammal which method comprises administering to a mammal in need thereof a therapeutically effective amount of at least one chemical as described herein for Formula I or a pharmaceutical composition as described herein.

Also provided is a method for potentiating cardiac myosin in a mammal which method comprises administering to a mammal in need thereof a therapeutically effective amount of at least one chemical entity as described herein for Formula I.

Also provided is the use, in the manufacture of a medicament for treating heart disease, of a chemical entity as described herein for Formula I.

In certain embodiments, the present invention provides methods of screening for compounds that will bind to myosin (for example, myosin II or β myosin), for example compounds that will displace or compete with the binding of at least one chemical entity having the structure of Formula I. The methods comprise combining an optionally-labeled compound of Formula I, myosin, and at least one candidate agent and determining the binding of the candidate agent to myosin.

In certain embodiments, the invention provides methods of screening for modulators of the activity of myosin. The methods comprise combining a compound of Formula I, myosin, and at least one candidate agent and determining the effect of the candidate agent on the activity of myosin.

Other embodiments will be apparent to those skilled in the art from the following detailed description.

As used in the present specification, the following words and phrases are generally intended to have the meanings as set forth below, except to the extent that the context in which they are used indicates otherwise. The following abbreviations and terms have the indicated meanings throughout:

μL=microliter
μM=micromolar
μ or μm r um=microns or micrometers
ATP=Adenosone triphosphate
ATPase=Adenosone triphosphatase
BSA=Bovine serum albumin
c-=Cyclo
cc=cubic centimeters
cm=centimeter
CBZ=carbobenzoxy=benzyloxycarbonyl
DIEA=N,N-diisopropylethylamine
DMF=N,N-dimethylformamide
DMSO=dimethyl sulfoxide
DTT=dithiothreitol
EGTA=ethyleneglycol-bis-(β-aminoethylether) N,N,N',N'-tetraacetic acid
EtOAc=ethyl acetate
EtOH=ethanol
g=Grams
h=Hour
HEPES=N-[2-hydroxyethyl]piperazine-N'-[2-ethanesulfonic acid]
Hz=Hertz
kg=kilogram
M=Molar
MHz=megahertz
min=Minute
mg=milligram
mL or ml=milliliter
mm=millimeters
mM=millimolar
NADH=nicotinamide-adenine dinucleotide—reduced form
nM=nanomolar
nm=nanometer
p-=Para
PEP=phosphoenolpyruvic acid
ph=Phenyl
PIPES=1,4-piperazine diethanesulfonic acid
ppm=parts per million
psi=Pounds per square inch
PyBroP=bromo-tris-pyrrolidinophosphonium hexafluorophosphate
QC=Quality control
RT=room temperature
s-=secondary
t-=Tertiary
THF=tetrahydrofuran
U=Units
WFI=water for injection
WFT=water for transfer As used in the present specification, the following words and phrases are generally intended to have the meanings as set forth below, except to the extent that the context in which they are used indicates otherwise.

As used herein, when any variable occurs more than one time in a chemical formula, its definition on each occurrence is independent of its definition at every other occurrence.

A dash ("-") that is not between two letters or symbols is used to indicate a point of attachment for a substituent. For example, —CONH$_2$ is attached through the carbon atom.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below. It will be understood by those skilled in the art with respect to any group containing one or more substituents that such groups are not intended to introduce any substitution or substitution patterns that are sterically impractical, synthetically non-feasible and/or inherently unstable.

"Alkyl" is intended to include linear, branched, or cyclic hydrocarbon structures and combinations thereof. Lower alkyl refers to alkyl groups of from 1 to 5 carbon atoms. Examples of lower alkyl groups include methyl, ethyl, propyl, isopropyl, butyl, s- and t-butyl and the like. Preferred alkyl groups are those of $C_{20}$ or below. More preferred alkyl groups are those of $C_{13}$ or below. Still more preferred alkyl groups are those of $C_6$ and below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl residues; it is intended to include cyclohexylmethyl, vinyl, allyl, isoprenyl and the like. Alkylene is another subset of alkyl, referring to the same residues as alkyl, but having two points of attachment. Examples of alkylene include ethylene (—$CH_2CH_2$—), propylene (—$CH_2CH_2CH_2$—), dimethylpropylene (—$CH_2C(CH_3)_2CH_2$—) and cyclohexylpropylene (—$CH_2CH_2CH(C_6H_{13})$—). When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

The term "alkoxy" or "alkoxyl" refers to the group —O-alkyl, for example, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

The term "substituted alkoxy" refers to the group —O-(substituted alkyl). One preferred substituted alkoxy group is "polyalkoxy" or —O-(optionally substituted alkylene)-(optionally substituted alkoxy), and includes groups such as —$OCH_2CH_2OCH_3$, and glycol ethers such as polyethyleneglycol and —$O(CH_2CH_2O)_xCH_3$, where x is an integer of about 2-20, or about 2-10, or about 2-5. Another preferred substituted alkoxy group is hydroxyalkoxy or —$OCH_2$($CH_2$)$_y$OH, where y is an integer of about 1-10, for example, about 1-4.

"Acyl" refers to groups of from 1 to 10 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. "Lower-acyl" refers to groups containing one to four carbons and "acyloxy" refers to the group O-acyl.

The term "amino" refers to the group —$NH_2$. The term "substituted amino" refers to the group —NHR or —NRR where each R is independently selected from the group: optionally substituted alkyl, optionally substituted alkoxy, optionally substituted amino, optionally substituted amidino, optionally substituted aryl, optionally substituted heteroaryl, optionally substituted heterocycloalkyl, optionally substituted acyl, optionally substituted alkoxycarbonyl, sulfanyl, sulfinyl and sulfonyl, e.g., diethylamino, methylsulfonylamino, dimethylaminosulfonyl, furanyl-oxy-sulfonamino.

The term "amidino" refers to the group —C(=NH)—$NH_2$. The term "substituted amidino" refers to the formula —C(=NR')—NR"R" in which each of the R" groups is independently chosen from hydrogen, optionally substituted alkyl, optionally substituted alkoxy, optionally substituted aminocarbonyl, optionally substituted aryl, optionally substituted heteroaryl, optionally substituted heterocyclyl, acyl, alkoxycarbonyl, sulfanyl, sulfinyl and sulfonyl and R' is chosen from hydrogen, cyano, optionally substituted alkyl, optionally substituted alkoxy, optionally substituted aminocarbonyl, optionally substituted aryl, optionally substituted heteroaryl, optionally substituted heterocyclyl, acyl, alkoxycarbonyl, sulfanyl, sulfinyl and sulfonyl, provided that at least one R' or R" group is not hydrogen.

"Aryl" encompasses: 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

"Aralkoxy" refers to the group —O-aralkyl. Similarly, "heteroaralkoxy" refers to the group —O-heteroaralkyl; "aryloxy" refers to —O-aryl; and "heteroaryloxy" refers to the group —O-heteroaryl.

"Aralkyl" refers to a residue in which an aryl moiety is attached to the parent structure via an alkyl residue. Examples include benzyl, phenethyl, phenylvinyl, phenylallyl and the like. "Heteroaralkyl" refers to a residue in which a heteroaryl moiety is attached to the parent structure via an alkyl residue. Examples include furanylmethyl, pyridinylmethyl, pyrimidinylethyl and the like.

"ATPase" refers to an enzyme that hydrolyzes ATP. ATPases include proteins comprising molecular motors such as the myosins.

"Halogen" or "halo" refers to fluorine, chlorine, bromine or iodine. Fluorine, chlorine and bromine are preferred. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heteroaryl" encompasses: 5- to 7-membered aromatic, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycloalkyl is not more than 1. Also included within the definition of heteroaryl are oxide derivatives, for example N-oxides of nitrogen containing rings, such as pyridine-1-oxide, S-oxides of sulfur containing rings, such as >S(O) and >S(O)$_2$ derivatives. Examples of heteroaryl groups include, but are not limited to, systems (as numbered from the linkage position assigned priority 1), such as 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

In the term "heteroarylalkyl" or "heteroaralkyl", heteroaryl and alkyl are as defined herein, and the point of attachment is on the alkyl group. This term encompasses, but is not limited to, pyridylmethyl, thiophenylmethyl, and (pyrrolyl)1-ethyl.

"Heterocycloalkyl" refers to a cycloalkyl residue in which one to four of the carbons is replaced by a heteroatom such as oxygen, nitrogen or sulfur. Also included are 4-, 5-, 6- or 7-membered non-aromatic rings containing 1-4 heteroatoms, bicyclic 8-, 9- or 10-membered non-aromatic ring systems containing 1-4 (or more) heteroatoms, or tricyclic 11- to 14-membered non-aromatic ring systems containing 1-4 (or more) heteroatoms; where the heteroatoms are selected from O, N or S. Examples include pyrrolidine, tetrahydrofuran, tetrahydro-thiophene, thiazolidine, piperidine, tetrahydropyran, tetrahydro-thiopyran, piperazine, morpholine, thiomorpholine and dioxane. Heterocycloalkyl also includes ring systems including unsaturated bonds, provided the number and placement of unsaturation does not render the group aromatic. Examples include imidazoline, oxazoline, tetrahydroisoquinoline, benzodioxan, benzodioxole and 3,5-dihydrobenzoxazinyl. Examples of substituted heterocycloalkyl include 4-methyl-1-piperazinyl and 4-benzyl-1-piperidinyl. Also included within the definition of heterocycloakly are oxide derivatives, for example N-oxides of nitrogen containing rings, such as pyridine-1-oxide, S-oxides of sulfur containing rings such as >S(O) and >S(O)$_2$ derivatives.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable adjuvant" refers to a compound that, when administered in conjunction with an antigen, augments the immune response to the antigen, but when administered alone does not generate an immune response to the antigen. Adjuvants can augment an immune response by several mechanisms including lymphocyte recruitment, stimulation of B and/or T cells, and stimulation of macrophages. Adjuvants include, for example, aluminum hydroxide, aluminum phosphate, MPL™, QS-21 (Stimulon™) or incomplete Freund's adjuvant. Pharmaceutical compositions may include a plurality of agents effective to induce an immune response.

Compounds of Formula I also include crystalline and amorphous forms of the compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Chemical entities of the present invention include, but are not limited to compounds of Formula I and all pharmaceutically acceptable forms thereof. Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, chelates, non-covalent complexes, prodrugs, and mixtures.

The term "pharmaceutically acceptable salt" refers to salts that retain the biological effectiveness and properties of the compounds of this invention and, which are not biologically or otherwise undesirable. In many cases, the compounds of this invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine.

In addition, if the compound of Formula I is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities, for example ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, and benzoate and like derivatives of functional groups (such as alcohol or amine groups) in the compounds of Formula I.

The term "solvate" refers to a compound (e.g., a compound of Formula I or a pharmaceutically acceptable salt thereof) in physical association with one or more molecules of a pharmaceutically acceptable solvent. It will be understood that phrases such as "a compound of Formula I or a pharmaceutically acceptable salt or solvate thereof" are intended to encompass the compound of Formula I, a pharmaceutically acceptable salt of the compound, a solvate of the compound, and a solvate of a pharmaceutically acceptable salt of the compound.

The term "chelate" refers to the chemical entity formed by the coordination of a compound to a metal ion at two (or more) points.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

"Substituted-" alkyl, aryl, heteroaryl and heterocycloalkyl refer respectively to alkyl, aryl, heteroaryl and heterocycloalkyl wherein one or more (up to about 5, for example, up to about 3) hydrogen atoms are replaced by a substituent independently selected from the group: acyl, optionally substituted alkyl (e.g., fluoroalkyl), optionally substituted alkoxy, alkylenedioxy (e.g. methylenedioxy), optionally substituted amino (e.g., alkylamino and dialkylamino), optionally substituted amidino, optionally substituted aryl (e.g., phenyl), optionally substituted aralkyl (e.g., benzyl), optionally substituted aryloxy (e.g., phenoxy), optionally substituted aralkoxy (e.g., benzyloxy), carboxy (—COOH), carboalkoxy (i.e., acyloxy or —OOCR), alkoxycarbonyl or carboxyalkyl (i.e., esters or —COOR), carboxamido, aminocarbonyl, benzyloxycarbonylamino (CBZ-amino), cyano, carbonyl, halogen, hydroxy, optionally substituted heteroaryl, optionally substituted heteroaralkyl, optionally substituted heteroaryloxy, optionally substituted heteroaralkoxy, nitro, sulfanyl, sulfinyl, sulfonyl, and thio.

The term "sulfanyl" refers to the groups: —S-(optionally substituted alkyl), —S-(optionally substituted aryl), —S-(optionally substituted heteroaryl), and —S-(optionally substituted heterocycloalkyl).

The term "sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocycloalkyl).

The term "sulfonyl" refers to the groups: —S($O_2$)—H, —S($O_2$)-(optionally substituted alkyl), —S($O_2$)-(optionally substituted amino), —S($O_2$)-(optionally substituted aryl), —S($O_2$)-(optionally substituted heteroaryl), —S($O_2$)-(optionally substituted heterocycloalkyl), —S($O_2$)-(optionally substituted alkoxy), —S($O_2$)-optionally substituted aryloxy), —S($O_2$)-(optionally substituted heteroaryloxy), and —S($O_2$)-(optionally substituted heterocycloalkyloxy).

The term "sulfuric diamide subunit" refers to the —NH—$SO_2$—NH— group. The term "substituted sulfuric diamide subunit" refers to the group —NR—$SO_2$—NH— or —NR—$SO_2$—NR— where each R is independently selected from optionally substituted alkyl.

The term "therapeutically effective amount" or "effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the particular compound of Formula I chosen, the dosing regimen to be followed, timing of administration, the manner of administration and the like, all of which can readily be determined by one of ordinary skill in the art.

The term "active agent" is used to indicate a chemical entity which has biological activity. In certain embodiments, an "active agent" is a compound having pharmaceutical utility.

By "significant" is meant any detectable change that is statistically significant in a standard parametric test of statistical significance such as Student's T-test, where $p<0.05$.

"Patient" refers to an animal, such as a mammal, for example a human, that has been or will be the object of treatment, observation or experiment. The methods of the invention can be useful in both human therapy and veterinary applications. In some embodiments, the patient is a mammal, and in some embodiments the patient is human.

"Treatment" or "treating" means any treatment of a disease in a patient, including:

a) preventing the disease, that is, causing the clinical symptoms of the disease not to develop;

b) inhibiting the disease;
slowing or arresting the development of clinical symptoms; and/or
relieving the disease, that is, causing the regression of clinical symptoms.

Certain embodiments of the invention include or employ at least one chemical entity having the structure of Formula I having the following combinations and permutations of substituent groups. These are presented in support of the appended claims to support other combinations and permutations of substituent groups, which for the sake of brevity have not been specifically claimed, but should be appreciated as encompassed within the teachings of the present disclosure. In that regard, the below-described subsets for each substituent are intended to apply to that substituent alone or in combination with one, several, or all of the described subsets for the other substituents.

The present invention is directed to at least one chemical entity that is a selective modulator of the cardiac sarcomere (e.g., by stimulating or otherwise potentiating the activity of cardiac myosin), as represented by Formula I:

Chemical entities of the invention can be synthesized utilizing techniques well known in the art, e.g., as illustrated below with reference to the Reaction Schemes.

Unless specified to the contrary, the reactions described herein take place at atmospheric pressure, generally within a temperature range from $-10°$ C. to $110°$ C. Further, except as employed in the Examples or as otherwise specified, reaction times and conditions are intended to be approximate, e.g., taking place at about atmospheric pressure within a temperature range of about $-10°$ C. to about $110°$ C. over a period of about 1 to about 24 hours; reactions left to run overnight average a period of about 16 hours.

The terms "solvent", "organic solvent" or "inert solvent" each mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like. Unless specified to the contrary, the solvents used in the reactions of the present invention are inert organic solvents. Unless specified to the contrary, for each gram of material, one cc (or mL) of solvent constitutes a volume equivalent.

The term "q.s." means adding a quantity sufficient to achieve a stated function, e.g., to bring a solution to the desired volume (i.e., 100%).

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by cyrstallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. For example, a compound of Formula I can be dissolved in a lower alkanol and placed on a Chiralpak AD (205×20 mm) column (Chiral Technologies, Inc.) conditioned for 60 min at 70% EtOAc in Hexane. It will be appreciated that where the desired enantiomer is converted into another chemical entity by one of the separation procedures described above, a further step may be required to liberate the desired enantiomeric form. Alternatively, a specific enantiomer may be synthesized by asymmetric synthesis using optically active reagents, substrates, catalysts or solvents, or by converting one enantiomer to the other by asymmetric transformation.

It will be appreciated by those skilled in the art that one or more of the reactants, steps and/or conditions described in the reaction schemes may require adjustment to accommodate various substituents at $R_1$ and $R_2$.

Many of the optionally substituted starting compounds 101, 103, 201, 301a and 301b and other reactants are commercially available, e.g., from Aldrich Chemical Company (Milwaukee, Wis.) or can be readily prepared by those skilled in the art using commonly employed synthetic methodology.

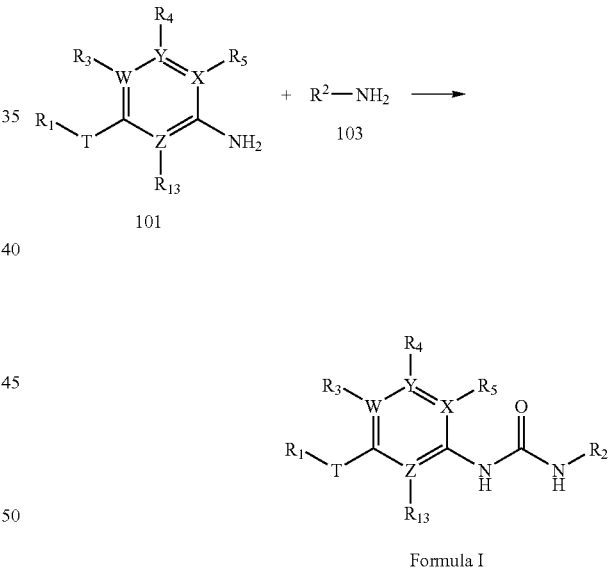

Referring to Reaction Scheme 1, a flask equipped with a magnetic stirrer, reflux condenser and thermal well, under nitrogen, is charged with phosgene or a phosgene equivalent (typically triphosgene) and a nonpolar, aprotic solvent such as dichloromethane or tetrahydrofuran. A solution of a compound of Formula 101 in a nonpolar, aprotic solvent such as dichloromethane or tetrahydrofuran is added dropwise over about 10-60 minutes and the solution is allowed to stir between 1 to 15 hr. A compound of Formula 103 is added portionwise, and the solution is stirred for about 10-60 min. A base, such as DIEA, is added dropwise for about one hour, and the solution is allowed to stir for about 1-15 hr. The product, a compound of Formula I, is isolated and purified.

REACTION SCHEME 2

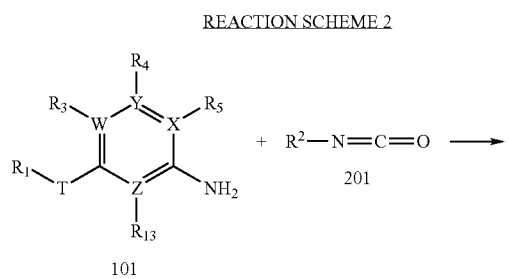

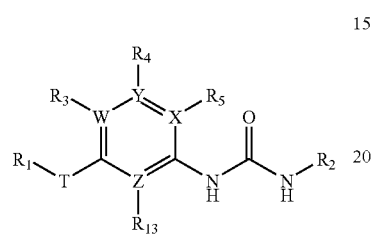

Formula I

Reaction Scheme 2 illustrates an alternative synthesis of compounds of Formula I. The isocyanate of Formula 201 can be formed and isolated independently from either corresponding amine (i.e., $R^2$—$NH_2$) using phosgene or a phosgene equivalent or from the corresponding carboxylic acid (i.e., $R^2$—COOH) using a Curtius or Hoffman rearrangement. A mixture of compounds of Formula 101 and 201 in an aprotic solvent such as dichloromethane or tetrahydrofuran from −40° C. to 110° C. is allowed to stir for between 1 to 15 hr. The product, a compound of Formula I, is isolated and optionally purified.

REACTION SCHEME 3

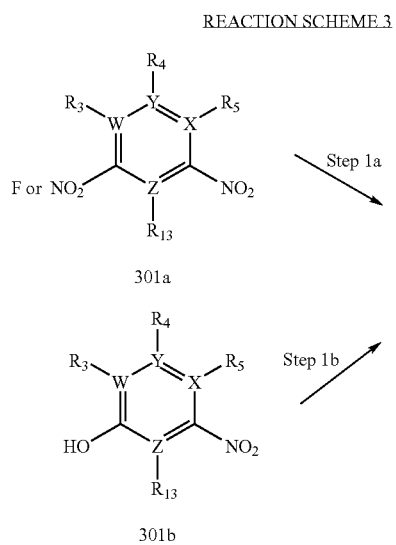

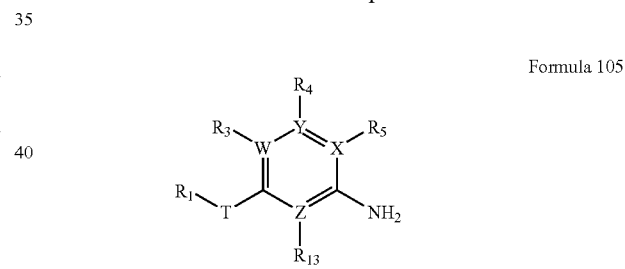

Referring to Reaction Scheme 3, Step 1a, a compound of Formula 301a is combined with about one equivalent of a compound of the formula $R_1$—OH wherein $R_1$ is as described above; a base such as potassium carbonate in an aprotic solvent such as DMF. The mixture is heated for about 1-16 hr at about 100° C. The product, a compound of Formula 303, is isolated and optionally purified.

Alternatively, as in Scheme 3, Step 1b, a compound of Formula 301b is combined a compound of the formula 105.

Formula 105

The mixture is stirred about 1-16 hr at about room temperature. The product, a compound of Formula 303, is isolated and purified. Alternatively, as in Scheme 3, Step 1b, a compound of Formula 301b is treated with a base such as sodium hydride in an aprotic solvent such as DMF for 1-16 hours from 0° C. to 110° C. A compound of the formula $R_1$-Q wherein $R_1$ is as described above and Q is a leaving group such as a halogen, methanesulfonate, a p-toluenesulfonate, or a trifluoromethanesulfonate in an aprotic solvent such as DMF or THF for 1-16 hours from 0° C. to 110° C. The product, a compound of Formula 303, is isolated and optionally purified.

Referring to Reaction Scheme 3, Step 2, a Parr hydrogenation bomb is charged with 10% Pd/C under a nitrogen atmosphere, followed by a solution of a compound of Formula 303 in a polar, protic solvent such as ethanol. The reaction is stirred for about 24 hr under about 70 psi $H_2$. The reaction mixture is filtered through celite and concentrated in vacuo to afford a compound of Formula 305, which can be carried forward to Formula I as illustrated with respect to Reaction Schemes 1 and 2.

REACTION SCHEME 4

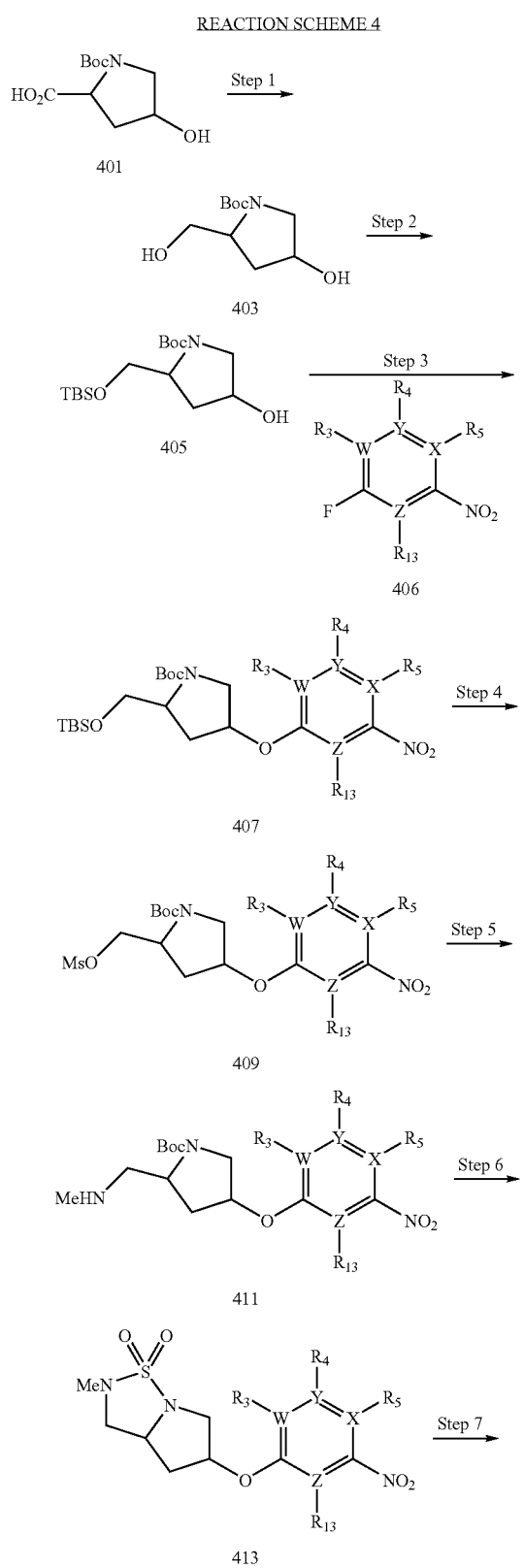

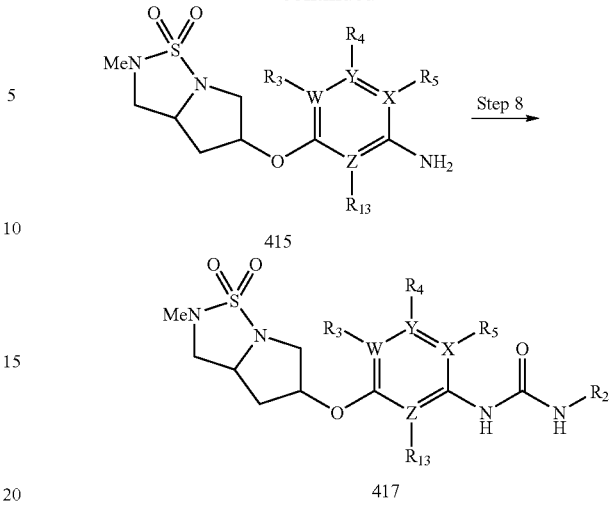

Referring to Reaction Scheme 4, Step 1, to a 0° C. suspension of an excess (such as about 2.0 equivalents) of a reducing agent, such as LiBH$_4$ in a suitable solvent such as THF is slowly added an excess (such as about 4.0 equivalents) of TMSCl. After stirring at room temperature for about 30 minutes, a compound of Formula 401 is added, and the resulting mixture is stirred at room temperature overnight. The product, a compound of Formula 403, is isolated and optionally purified.

Referring to Reaction Scheme 4, Step 2, to a 0° C. solution of a compound of Formula 403 and a base, such as Et$_3$N in a suitable solvent such as dichloromethane is added an excess (such as about 1.05 equivalents) of TBSCl, followed by a few crystals of DMAP. The solution is allowed to warm to room temperature and stirred overnight. The product, a compound of Formula 405, is isolated and used without further purification.

Referring to Reaction Scheme 4, Step 3, to a 0° C. solution of a compound of Formula 405 in a suitable solvent such as DMF is added a base such as an excess (such as about 1.3 equivalents) of NaH. After stirring for about 30 minutes at about 0° C., an excess (such as about 1.2 equivalents) of a compound of Formula 406 is added. The reaction mixture is allowed to warm to room temperature and stirred overnight. The product, a compound of Formula 407, is isolated and optionally purified.

Referring to Reaction Scheme 4, Step 4, to a solution of a compound of Formula 407 in a polar, protic solvent such as methanol is added aqueous acid, such as 1N hydrochloric acid. After about 1 h, the reaction is quenched by the addition of base, such as solid NaHCO$_3$. The resulting alcohol is dissolved in a suitable solvent such as THF, and a base such as Et$_3$N is added. After the solution is cooled to 0° C., an excess (such as about 1.05 equivalents) of MsCl is added dropwise. The reaction is then allowed to warm to room temperature. The product, a compound of Formula 409, is isolated and optionally purified.

Referring to Reaction Scheme 4, Step 5, to a solution of a compound of Formula 409 in a suitable solvent such as THF is added an excess of methylamine (such as 40% aqueous methylamine). The resulting solution is heated to about 55° C. The product, a compound of Formula 411, is isolated and used without further purification.

Referring to Reaction Scheme 4, Step 6, to a solution of a compound of Formula 411 in a suitable solvent such as dichloromethane is added trifluoroacetic acid, and the mixture is stirred for about 1 h. The desired diamine is isolated and used immediately. To a cooled (about −10° C.) solution of the diamine in a suitable solvent such as dichloromethane is added an excess (such as about 1.05 equivalents) of sulfuryl chloride while maintaining the reaction temperature below 0° C. A base, such as diisopropylethylamine is then added dropwise, and the reaction is allowed to warm to room temperature. The product, a compound of Formula 413, is isolated and optionally purified.

Referring to Reaction Scheme 4, Step 7, a suspension of a compound of Formula 413 and 10% Pd/C in a suitable solvent such as MeOH is placed in a Parr bomb and pressurized with hydrogen gas (such as at about 60 psi). After about 3 h, the product, a compound of Formula 415, is isolated and optionally purified.

Referring to Reaction Scheme 4, Step 8, to a compound of Formula 415 in a suitable solvent such as THF is added an excess (such as about 1.1 equivalents) of a compound of formula $R_2NCO$. The reaction is allowed to stir overnight. The product, a compound of Formula 417, is isolated and optionally purified.

As discussed above, a specific enantiomer of Formula I can be synthesized by asymmetric synthesis using optically active reagents, substrates, catalysts or solvents, or by converting one enantiomer to the other by asymmetric transformation. For example, (R)- and (S)-3-hydroxypiperidine are commercially available are commercially available from Sigma-Aldrich, as are (R)- and (S)-hydroxypyrrolidine; they can also be resolved [e.g., using (6,6-dimethyl-2-oxo-adamantan-1-yl)-methane sulfonic acid, see: Ringdahl et al., *J. Chem. Soc. Perkin Trans. II*, 1981, 4, 697-8] and via other published methodology. Additional asymmetric synthetic approaches can be employed as illustrated in Reaction Schemes 5 and 6, in which PG represents an orthogonal protecting group (or a hydrogen, depending on the stage of synthesis, as will be appreciated by those skilled in the art), LG represents a leaving group, and n is 1, 2 or 3. These protecting and leaving groups can be readily inserted and removed by those skilled in the art using commonly employed synthetic methodology.

REACTION SCHEME 5

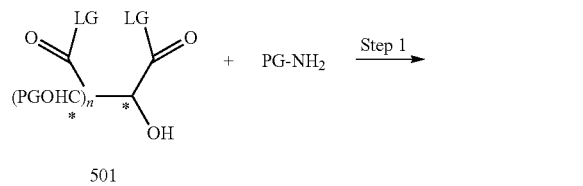

501

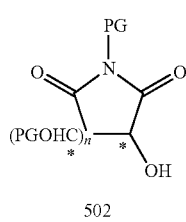

502

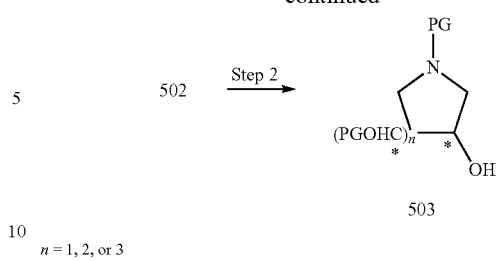

503

$n = 1, 2, \text{ or } 3$

Referring to Reaction Scheme 5, Steps 1 and 2, a compound of Formula 501 is combined with about 1 equivalent of a protected amine of Formula 502 (such as benzyl amine) in a solvent such as dichloromethane or DMF. The reaction takes place at −20° C. to 100° C. over a period of 1 to 48 hours. The product, a compound of Formula 503, is isolated conventionally and then treated with a reducing agent (such as lithium aluminum hydride or borane) in an aprotic solvent such as THF. The reaction takes place at −20° C. to 100° C. over a period of 1 to 48 hours. The product, a compound of Formula 503, is then isolated conventionally, and can be carried forward to chemical entities having the structure of Formula I, e.g., as described above.

REACTION SCHEME 6

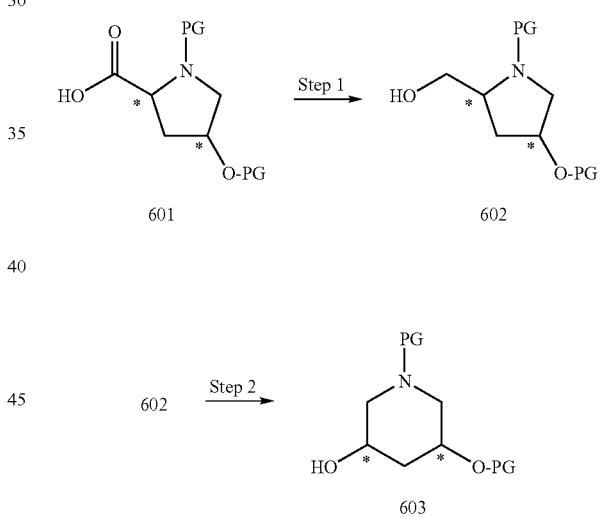

Referring to Reaction Scheme 6, Step 1, a compound of Formula 601 is treated with a reducing agent (such as lithium aluminum hydride or lithium borohydride) in solvent such as THF. The reaction takes place at −20° C. to 100° C. over a period of 1 to 48 hours. The product, a compound of Formula 602, is isolated conventionally.

Referring to Reaction Scheme 6, Step 2, a compound of formula 602 is stirred with an acylating agent, such as trifluoroacetic anhydride in a solvent, such as THF from −78° C. to 70° C. for 1 to 12 hours. After addition of a base, such as triethylamine, the mixture is stirred at 20° C. to reflux from 8 to 48 hours. The product, a compound of Formula 603, is isolated conventionally (see, e.g., U.S. Pat. No. 6,316,626) and can be carried forward to chemical entities having the structure of Formula I, e.g., as described above.

Reaction Scheme 7

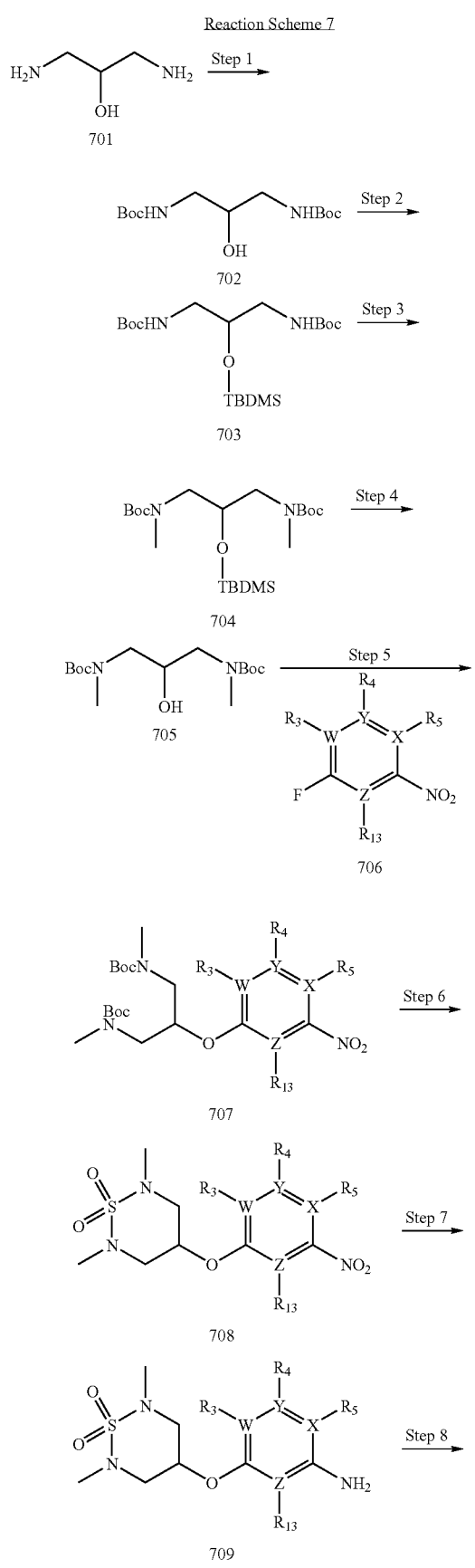
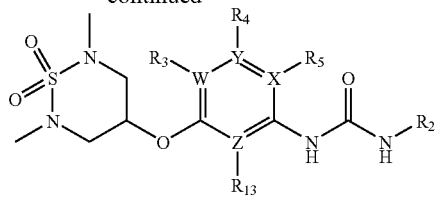

Referring to Reaction Scheme 7, Step 1, to a 0° C. suspension of a suitable diaminoalcohol, such as 1,3-diaminopropan-2-ol and a suitable base, such as NaOH (about 2.4 equivalents) in a suitable solvent, such as THF and $H_2O$ is added an excess (about 2.2 equivalents) of a suitable protecting reagent, such as $Boc_2O$. The reaction mixture is warmed to RT and stirred overnight. The product, a compound of Formula 702, is isolated and optionally purified.

Referring to Reaction Scheme 7, Step 2, to a 0° C. solution of a compound of Formula 702 and an excess (about 2.5 equivalents) of a suitable base such as imidazole and a suitable solvent, such as DMF, is added an excess (about 1.2 equivalents) of suitable protecting reagent, such as t-butyldimethylsilylchloride (TBDSMCl). The reaction is warmed to RT and stirred for about 2 hours. The product, a compound of Formula 703, is isolated and optionally purified.

Referring to Reaction Scheme 7, Step 3, to a 0° C. solution of a compound of Formula 703 in a suitable solvent, such as DMF, is added an excess (about 2.4 equivalents) of a suitable base, such as sodium hydride. After stirring for a suitable time, about 30 minutes, an excess (about 2.4 equivalents) of an alkylating reagent, such as methyl iodide, is added. The reaction is stirred for about 2 hours and the product, and a compound of Formula 704, is isolated and optionally purified.

Referring to Reaction Scheme 7, Step 4, to a 0° C. solution of a compound of Formula 704 in a suitable solvent, such as methanol is added a suitable acid, such as concentrated HCl and the reaction mixture is stirred at RT for a suitable time, such as about 6 hrs. The product, a compound of Formula 705, is isolated and optionally purified.

Referring to Reaction Scheme 7, Step 5, to a 0° C. solution of a compound of Formula 705, an excess (about 1.6 equivalents) of a compound of Formula 706, and a suitable solvent, such as DMF is added an excess (about 1.28 equivalents) of a suitable base, such as of NaH. The resultant mixture is stirred at 0° C. for about 30 min and $H_2O$ is added. The product, a compound of Formula 707, is isolated and optionally purified.

Referring to Reaction Scheme 7, Step 6, a solution of 4.6 g (10 mmol) a compound of Formula 707, a suitable solvent, such as methanol, and a suitable acid, such HCl is stirred at RT for about 1 hour and concentrated. To the concentrated residue, a suitable solvent, such as DCM at 0° C., and an excess (about 4 equivalents) of a suitable base, such as diisopropylethyl amine (DIEA), is added about 1 equivalent of $SO_2Cl_2$ and reaction mixture is stirred overnight at RT. The product, a compound of Formula 708, is isolated and optionally purified.

Referring to Reaction Scheme 7, Step 7, a compound Formula 708, a suitable solvent, such as MeOH, and a suitable amount of 10% Pd/C, is charged with a suitable about of $H_2$, about 45 psi, and stirred for about 1 hour. The product, a compound of Formula 709, is isolated and optionally purified.

Referring to Reaction Scheme 7, Step 8, a compound of Formula 709 in a suitable solvent, such as DCM and DMF is added about 1 equivalent of a compound of the formula $R_2NCO$ and stirred for about 10 minutes. The product, a compound of Formula 710, is isolated and optionally purified.

Compounds prepared by the above-described process of the invention can be identified, e.g., by the presence of a detectable amount of Formula 101, 103, 201, 305, 401, 406, 403, 405, and the like. While it is well known that pharmaceuticals must meet pharmacopoeia standards before approval and/or marketing, and that synthetic reagents (such as the various substituted amines or alcohols) and precursors should not exceed the limits prescribed by pharmacopoeia standards, final compounds prepared by a process of the present invention may have minor, but detectable, amounts of such materials present, for example at levels in the range of 95% purity with no single impurity greater than 1%. These levels can be detected, e.g., by emission spectroscopy. It is important to monitor the purity of pharmaceutical compounds for the presence of such materials, which presence is additionally disclosed as a method of detecting use of a synthetic process of the invention.

A racemic mixture of isomers of a compound of Formula I is optionally placed on a chromatography column and separated into (R)- and (S)-enantiomers.

A compound of Formula I is optionally contacted with a pharmaceutically acceptable acid to form the corresponding acid addition salt.

A pharmaceutically acceptable acid addition salt of Formula I is optionally contacted with a base to form the corresponding free base of Formula I.

Provided is at least one chemical entity chosen from compounds of Formula I

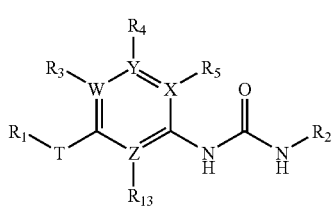

Formula I and pharmaceutically acceptable salts, solvates, chelates, non-covalent complexes, prodrugs, and mixtures thereof, wherein T is selected from —O—, —O-(optionally substituted lower alkylene)-, -(optionally substituted lower alkylene)-O—, —S—, —S-(optionally substituted lower alkylene)-, -(optionally substituted lower alkylene)-S—, —$SO_2$—, —$SO_2$-(optionally substituted lower alkylene)-, and -(optionally substituted lower alkylene)-$SO_2$—;

W, X, Y, and Z are independently selected from —C═ and —N═, provided that no more than two of W, X, Y, and Z are —N═;

$R_1$ is selected from optionally substituted alkyl, optionally substituted amino, optionally substituted aryl, optionally substituted heteroaryl, and optionally substituted heterocycloalkyl;

$R_2$ is selected from optionally substituted aryl, optionally substituted aralkyl; optionally substituted cycloalkyl, optionally substituted heteroaryl, optionally substituted heteroaralkyl and optionally substituted heterocycloalkyl;

$R_3$ is selected from hydrogen, halo, cyano, nitro, optionally substituted alkyl, optionally substituted heterocycloalkyl, and optionally substituted heteroaryl when W is —C═, and $R_3$ is absent when W is —N═;

$R_4$ is selected from hydrogen, halo, cyano, nitro, optionally substituted alkyl, optionally substituted heterocycloalkyl, and optionally substituted heteroaryl when Y is —C═, and $R_4$ is absent when Y is —N═; and $R_5$ is selected from hydrogen, halo, cyano, nitro, optionally substituted alkyl, optionally substituted heterocycloalkyl, and optionally substituted heteroaryl when X is —C═, and $R_5$ is absent when X is —N═;

$R_6$ and $R_7$ are independently selected from hydrogen, optionally substituted alkyl, optionally substituted cycloalkyl, optionally substituted heteroalkyl, optionally substituted heterocycloalkyl, optionally substituted aryl and optionally substituted heteroaryl;

$R_{13}$ is selected from hydrogen, halo, cyano, nitro, hydroxyl, optionally substituted alkyl, optionally substituted heterocycloalkyl, and optionally substituted heteroaryl when Z is —C═, and $R_{13}$ is absent when Z is —N═; and;

provided that:

if $R_3$ is hydrogen, halo or optionally substituted heteroaryl, then one of $R_{13}$ and $R_5$ is other than hydrogen, or W or X is —N═, or two of W, X, Y, and Z are —N═, or $R_1$ is optionally substituted alkyl or optionally substituted heterocycloalkyl comprising an optionally substituted sulfuric diamide subunit;

if $R_4$ is hydrogen, halo, nitro or optionally substituted heteroaryl, then one of $R_{13}$ and $R_5$ is other than hydrogen, or W or X is —N═, or two of W, X, Y, and Z are —N═, or $R_1$ is optionally substituted alkyl or optionally substituted heterocycloalkyl comprising an optionally substituted sulfuric diamide subunit; or if W, X, Y, and Z are —C═, or if X and W are both —C═ and one of Y and Z is —N═, then one of $R_{13}$ and $R_5$ is other than hydrogen, or $R_3$ is not hydrogen, halo or optionally substituted heteroaryl, or $R_4$ is not hydrogen, halo, nitro or optionally substituted heteroaryl, or $R_1$ is optionally substituted alkyl or optionally substituted heterocycloalkyl comprising an optionally substituted sulfuric diamide subunit;

and further provided that if $R_1$ is amino or if $R_1$ is heteroaryl or heterocycloalkyl with a heteroatom bonded to T, then T is not —O—, —S—, —O-alkyl, or —S-alkyl.

In some embodiments, one of W, X, Y, and Z is —N═.

In some embodiments, W, X, Y, and Z are —C═.

In some embodiments, $R_6$ and $R_7$ are both hydrogen.

In some embodiments, one of $R_6$ and $R_7$ is lower alkyl.

In some embodiments, one of $R_6$ and $R_7$ is lower alkyl and the other is hydrogen.

In some embodiments, $R_1$ is selected from optionally substituted alkyl; optionally substituted piperazinyl; optionally substituted 1,1-dioxo-1$\lambda^6$-[1,2,5]thiadiazolidinyl; optionally substituted 1,1-dioxo-1$\lambda^6$-[1,2,6]thiadiazinanyl; optionally substituted 1,1-dioxo-1$\lambda^6$-2,3,3a,4,5,6-hexahydropyrrolo[1,2-b][1,2,5]thiadiazolyl; optionally substituted 3-oxo-tetrahydro-pyrrolo[1,2-c]oxazol-6-yl; optionally substituted 2-oxo-imidazolidin-1-yl; optionally substituted morpholinyl; optionally substituted 1,1-dioxo-1$\lambda^6$-thiomorpholin-4-yl; optionally substituted pyrrolidinyl; optionally substituted piperidinyl; optionally substituted azepanyl; optionally substituted 1,4-diazepanyl; optionally substituted 3-oxo-tetrahydro-1H-oxazolo[3,4-a]pyrazin-3(5H)-one; optionally substituted 5,6,7,8-tetrahydro-[1,2,4]triazolo[4,3-a]pyrazinyl, and optionally substituted

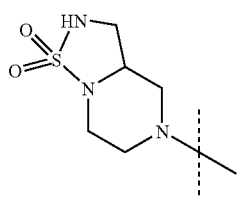

In some embodiments, $R_1$ is
lower alkyl optionally substituted with one or two groups chosen from optionally substituted alkoxy and optionally substituted amino;
optionally substituted piperazinyl;
optionally substituted piperidinyl;
optionally substituted pyrrolidinyl;
optionally substituted 3-oxo-tetrahydro-pyrrolo[1,2-c]oxazol-6-yl;
optionally substituted 1,1-dioxo-$1\lambda^6$-[1,2,5]thiadiazolidin-2-yl;
optionally substituted 1,1-dioxo-$1\lambda^6$-[1,2,5]thiadiazolidin-3-yl;
optionally substituted 1,1-dioxo-$1\lambda^6$-[1,2,6]thiadiazinan-4-yl;
optionally substituted 1,1-dioxo-$1\lambda^6$-2,3,3a,4,5,6-hexahydropyrrolo[1,2-b][1,2,5]thiadiazol-4-yl;
optionally substituted 1,1-dioxo-$1\lambda^6$-2,3,3a,4,5,6-hexahydropyrrolo[1,2-b][1,2,5]thiadiazol-5-yl;
optionally substituted azepanyl, or
optionally substituted 1,4-diazepanyl.

In some embodiments, $R_1$ is selected from
optionally substituted 2-alkoxyethyl,
optionally substituted (1-carboxamidocyclopentyl)methyl,
optionally substituted 2-carboxamidoethyl,
optionally substituted 2-alkoxycarbonylaminoethyl,
optionally substituted 2-carboxamidoethyl,
optionally substituted 2-(sulfamoylamino)ethyl,
optionally substituted 2-(alkylsulfonamido)ethyl,
optionally substituted 2-guanidinoethyl,
optionally substituted 2-aminoethyl,
optionally substituted 1-acyl-pyrrolidin-3-yl,
optionally substituted 1-alkoxycarbonyl-pyrrolidin-3-yl,
optionally substituted 1-amidino-pyrrolidin-3-yl,
optionally substituted 1-sulfonyl-pyrrolidin-3-yl,
optionally substituted 3-oxo-tetrahydro-pyrrolo[1,2-c]oxazol-6-yl,
1-acyl-piperidin-3-yl,
optionally substituted 1-alkoxycarbonyl-piperidin-3-yl,
optionally substituted 1-amidino-piperidin-3-yl,
optionally substituted 1-sulfonyl-piperidin-3-yl,
1,1-dioxo-$1\lambda^6$-[1,2,5]thiadiazolidin-2-yl substituted with one or more lower alkyl groups, such as methyl groups;
1,1-dioxo-$1\lambda^6$-[1,2,5]thiadiazolidin-3-yl substituted with one or more lower alkyl groups, such as methyl groups;
1,1-dioxo-$1\lambda^6$-[1,2,6]thiadiazinan-4-yl substituted with one or more lower alkyl groups, such as methyl groups;
1,1-dioxo-$1\lambda^6$-2,3,3a,4,5,6-hexahydropyrrolo[1,2-b][1,2,5]thiadiazol-4-yl substituted with one or more lower alkyl groups, such as methyl groups; and
1,1-dioxo-$1\lambda^6$-2,3,3a,4,5,6-hexahydropyrrolo[1,2-b][1,2,5]thiadiazol-5-yl substituted with one or more lower alkyl groups, such as methyl groups.

In some embodiments, $R_1$ is selected from 1-methoxypropan-2-yl, (1-acetamidocyclopentyl)methyl, 2-acetamido-2-methylprop-1-yl, 2-(methoxycarbonylamino)eth-1-yl, 2-(tert-butoxycarbonyl(methyl)amino)eth-1-yl, 1-(methoxycarbonyl(methyl)amino)propan-2-yl, 1-(tert-butoxycarbonyl(methyl)amino)propan-2-yl, 2-acetamidoeth-1-yl, 2-(N-methylacetamido)eth-1-yl, 1-(N-methylacetamido)propan-2-yl, 2-(N,N-dimethylsulfamoylamino)eth-1-yl, 2-((N,N-dimethylsulfamoyl)(methyl)amino)eth-1-yl, 1-((N,N-dimethylsulfamoyl)(methyl)amino)propan-2-yl, 2-(ethylsulfonamido)eth-1-yl, 2-(N-methylethylsulfonamido)eth-1-yl, 1-(N-methylethylsulfonamido)propan-2-yl, 1-(N-methylpropan-2-ylsulfonamido)propan-2-yl, 2-(N-methylpropan-2-ylsulfonamido)eth-1-yl, 2-(2-cyano-1,3,3-trimethylguanidino)eth-1-yl, 2-(methylamino)eth-1-yl, 1-acetyl-piperidin-3-yl, 1-methoxyacetyl-piperidin-3-yl, 1-(azetidine-1-carbonyl)-piperidin-3-yl, 1-methoxycarbonyl-piperidin-3-yl, 1-ethoxycarbonyl-piperidin-3-yl, 1-dimethylaminocarbonyl-piperidin-3-yl, 1-sulfonyl-piperidin-3-yl, 1-methanesulfonyl-piperidin-3-yl, 1-(ethane-2-sulfonyl)-piperidin-3-yl, 1-(propane-2-sulfonyl)-piperidin-3-yl, 1-(azetidin-1-yl-sulfonyl)-piperidin-3-yl, 1-dimethylaminosulfonyl-piperidin-3-yl, 1-($N^1$-azetidin-1-yl-$N^2$-cyano-amidino)-piperidin-3-yl, 1-($N^2$-cyano-$N^1$,$N^1$-dimethyamidino)-piperidine-3-yl, 1-acetyl-pyrrolidin-3-yl, 1-methoxyacetyl-pyrrolidin-3-yl, 1-(azetidine-1-carbonyl)-pyrrolidin-3-yl, 1-methoxycarbonyl-pyrrolidin-3-yl, 1-methoxycarbonyl-2-methoxymethyl-pyrrolidin-4-yl, 1-sulfonyl-pyrrolidin-3-yl, 1-methanesulfonyl-pyrrolidin-3-yl, 1-(ethane-2-sulfonyl)-pyrrolidin-3-yl, 1-(ethane-2-sulfonyl)-4-methoxy-pyrrolidin-3-yl, 1-(ethane-2-sulfonyl)-5-methoxymethyl-pyrrolidin-3-yl, 1-(propane-2-sulfonyl)-pyrrolidin-3-yl, 1-(azetidin-1-yl-sulfonyl)-pyrrolidin-3-yl, 1-dimethylaminosulfonyl-pyrrolidin-3-yl, 1-dimethylaminosulfonyl-2-methoxymethyl-pyrrolidin-4-yl, 1-($N^1$-azetidin-1-yl-$N^2$-cyano-amidino)-pyrrolidin-3-yl, 1-($N^2$-cyano-$N^1$,$N^1$-dimethyamidino)-pyrrolidin-3-yl, or 3-oxo-tetrahydro-pyrrolo[1,2-c]oxazol-6-yl, or 5-methyl-1,1-dioxo-$1\lambda^6$-[1,2,5]thiadiazolidin-2-yl; 5-methyl-1,1-dioxo-$1\lambda^6$-[1,2,5]thiadiazolidin-3-yl; 2,6-dimethyl-1,1-dioxo-$1\lambda^6$-[1,2,6]thiadiazinan-4-yl; 2-methyl-1,1-dioxo-$1\lambda^6$-3,3a,4,5,6-pentahydropyrrolo[1,2-b][1,2,5]thiadiazol-4-yl, 2-methyl-1,1-dioxo-$1\lambda^6$-3,3a,4,5,6-pentahydropyrrolo[1,2-b][1,2,5]thiadiazol-5-yl,

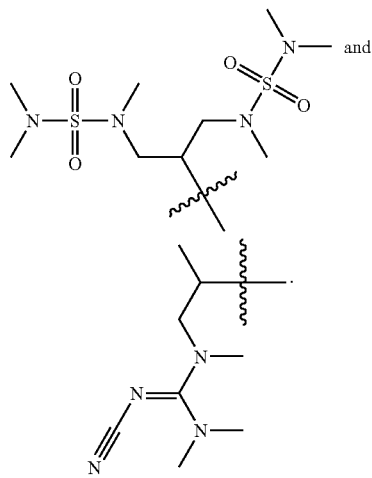

In some embodiments, $R_1$ is selected from 2-(methoxycarbonylamino)eth-1-yl, 1-(methoxycarbonyl(methyl)amino)propan-2-yl, 2-acetamido-2-methylprop-1-yl, 2-(N,N-dimethylsulfamoylamino)eth-1-yl, 2-((N,N-dimethylsulfamoyl)(methyl)amino)eth-1-yl, 1-((N,N-dimethylsulfamoyl)

(methyl)amino)propan-2-yl, 2-(ethylsulfonamido)eth-1-yl, 2-(N-methylethylsulfonamido)eth-1-yl, 1-(N-methylethylsulfonamido)propan-2-yl, 1-(N-methylpropan-2-ylsulfonamido)propan-2-yl, 2-(N-methylpropan-2-ylsulfonamido)eth-1-yl, 1-acetyl-pyrrolidin-3-yl, 1-methoxycarbonyl-2-methoxymethyl-pyrrolidin-4-yl, 1-sulfonyl-pyrrolidin-3-yl, 1-(ethane-2-sulfonyl)-pyrrolidin-3-yl, 1-(ethane-2-sulfonyl)-5-methoxymethyl-pyrrolidin-3-yl, 1-dimethylaminosulfonyl-pyrrolidin-3-yl, 1-dimethylaminosulfonyl-2-methoxymethyl-pyrrolidin-4-yl, 3-oxo-tetrahydro-pyrrolo[1,2-c]oxazol-6-yl, 1-methoxycarbonyl-piperidin-3-yl, 1-ethoxycarbonyl-piperidin-3-yl, 1-sulfonyl-piperidin-3-yl, 1-methanesulfonyl-piperidin-3-yl, and 1-(ethane-2-sulfonyl)-piperidin-3-yl, and 2-methyl-1,1-dioxo-1$\lambda^6$-3,3a,4,5,6-pentahydropyrrolo[1,2-b][1,2,5]thiadiazol-5-yl.

In some embodiments, $R_1$ is chosen from optionally substituted alkyl and optionally substituted heterocycloalkyl comprising an optionally substituted sulfuric diamide subunit.

In some embodiments, $R_1$ is optionally substituted alkyl. In some embodiments, $R_1$ is optionally substituted lower alkyl. In some embodiments, $R_1$ is lower alkyl substituted with one or two groups chosen from optionally substituted alkoxy and optionally substituted amino. In some embodiments, $R_1$ is lower alkyl substituted with one or two groups chosen from alkylsulfonylamino, carboxamido, optionally substituted aminosulfonylamino, and alkoxycarbonylamino.

In some embodiments, $R_1$ is optionally substituted heterocycloalkyl comprising an optionally substituted sulfuric diamide subunit. In some embodiments, $R_1$ is optionally substituted 1,1-dioxo-1$\lambda^6$-[1,2,5]thiadiazolidinyl; 1,1-dioxo-1$\lambda^6$-[1,2,6]thiadiazinanyl; and 1,1-dioxo-1$\lambda^6$-2,3,3a,4,5,6-hexahydropyrrolo[1,2-b][1,2,5]thiadiazolyl. In some embodiments, $R_1$ is chosen from 1,1-dioxo-1$\lambda^6$-[1,2,5]thiadiazolidinyl; 1,1-dioxo-1$\lambda^6$-[1,2,6]thiadiazinanyl; and 1,1-dioxo-1$\lambda^6$-2,3,3a,4,5,6-hexahydropyrrolo[1,2-b][1,2,5]thiadiazolyl, each of which is substituted with one or more lower alkyl groups. In some embodiments, $R_1$ is chosen from 1,1-dioxo-1$\lambda^6$-[1,2,5]thiadiazolidinyl; 1,1-dioxo-1$\lambda^6$-[1,2,6]thiadiazinanyl; and 1,1-dioxo-1$\lambda^6$-2,3,3a,4,5,6-hexahydropyrrolo[1,2-b][1,2,5]thiadiazolyl, each of which is substituted with one or more methyl groups.

In some embodiments, $R_1$ is optionally substituted

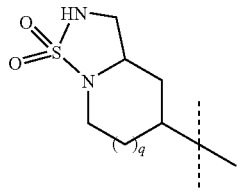

wherein q is chosen from 0 and 1. In some embodiments, $R_1$ is

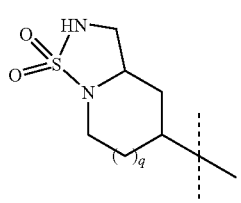

wherein q is chosen from 0 and 1 and wherein the bicyclic ring system is optionally substituted with one or two groups chosen from halo, hydroxy, cyano, carboxy, alkoxycarbonyl, optionally substituted amino, optionally substituted aminocarbonyl, optionally substituted lower alkyl, and optionally substituted lower alkoxy. In certain embodiments, the bicyclic ring system is optionally substituted with one or two groups chosen from halo, hydroxy, optionally substituted lower alkyl, and optionally substituted lower alkoxy. In certain embodiments, the bicyclic ring system is optionally substituted with one or two groups chosen from halo, hydroxy, lower alkyl, and lower alkoxy. In certain embodiments, the bicyclic ring system is optionally substituted with one or two lower alkyl groups.

In some embodiments, $R_1$ is optionally substituted

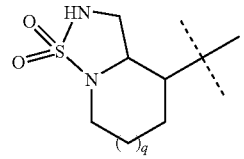

wherein q is chosen from 0 and 1. In some embodiments, $R_1$ is

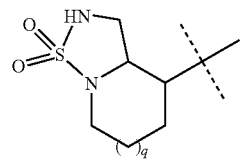

wherein q is chosen from 0 and 1 and wherein the bicyclic ring system is optionally substituted with one or two groups chosen from halo, hydroxy, cyano, carboxy, alkoxycarbonyl, optionally substituted amino, optionally substituted aminocarbonyl, optionally substituted lower alkyl, and optionally substituted lower alkoxy. In certain embodiments, the bicyclic ring system is optionally substituted with one or two groups chosen from halo, hydroxy, optionally substituted lower alkyl, and optionally substituted lower alkoxy. In certain embodiments, the bicyclic ring system is optionally substituted with one or two groups chosen from halo, hydroxy, lower alkyl, and lower alkoxy. In certain embodiments, the bicyclic ring system is optionally substituted with one or two lower alkyl groups.

In some embodiments, $R_2$ is selected from optionally substituted aryl, optionally substituted substituted aralkyl, optionally substituted cycloalkyl, optionally substituted heteroaryl, optionally substituted heteroaralkyl, and optionally substituted heterocycloalkyl.

In some embodiments, where $R_2$ is represented by the formula -$T_3$-$R_{21}$ where:
$T_3$ is $C_1$ to $C_3$ straight or branched-chain alkylene; and
$R_{21}$ is selected from tetrahydrofuranyl, tetrahydropyranyl, optionally substituted pyrrolidinyl, optionally substituted morpholinyl, optionally substituted piperidinyl, optionally substituted pyridinyl and optionally substituted pheny.

In some embodiments, $R_2$ is represented by the formula -$T_3$-$R_{21}$ where:
-$T_3$ is methylene; and
$R_{21}$ is selected from tetrahydrofuran-2-yl, tetrahydrofuran-3-yl, N-acyl-pyrrolidin-2-yl, N-acyl-morpholin-3-yl, N-acylpiperidin-3-yl, N-acyl-piperidin-4-yl, pyridin-3-yl, pyridin-4-yl, optionally substituted piperidinyl, p-methoxy-phenyl, and p-fluoro-phenyl.

In some embodiments, $R^2$ is selected from $R_2$ is selected from optionally substituted tetrahydrofuranyl, optionally substituted piperidinyl, optionally substituted morpholinyl, optionally substituted cyclohexyl, optionally substituted pyrrolidinyl, optionally substituted phenyl, optionally substituted naphthyl, optionally substituted pyrrolyl, optionally substituted thiazolyl, optionally substituted isoxazolyl, optionally substituted pyrazolyl, optionally substituted oxazolyl, optionally substituted 1,3,4-oxadiazolyl, optionally substituted pyridinyl, optionally substituted pyrazinyl, optionally substituted pyrimidinyl and optionally substituted pyridazinyl.

In some embodiments, $R_2$ is chosen from pyridin-3-yl optionally substituted with lower alkyl; pyridin-4-yl optionally substituted with lower alkyl; phenyl optionally substituted with halo; optionally substituted pyrimidin-5-yl; or optionally substituted isoxazol-3-yl, tetrahydrofuran-2-yl, tetrahydrofuran-3-yl, N-acyl-pyrrolidin-2-yl, N-acyl-morpholin-3-yl, N-acyl-piperidin-3-yl, N-acyl-piperidin-4-yl and cyclohexyl.

In some embodiments, $R_3$ is hydrogen, cyano, fluoro, chloro, or methyl.

In some embodiments, $R_4$ and $R_5$ are independently chosen from hydrogen, pyridinyl, halo and optionally substituted lower alkyl.

In some embodiments, $R_4$ is hydrogen, pyridinyl, trifluoromethyl, or fluoro.

In some embodiments, $R_5$ is hydrogen, chloro, fluoro, methyl, or trifluoromethyl.

In some embodiments, $R_{13}$ is hydrogen, halo, hydroxyl, or lower alkyl.

In some embodiments, $R_{13}$ is hydrogen or fluoro.

In some embodiments, one of $R_3$, $R_4$, $R_5$, and $R_{13}$ is halo, methyl or cyano and the others are hydrogen.

In some embodiments, two of $R_3$, $R_4$, $R_5$, and $R_{13}$ are halo or cyano and the others are hydrogen.

In some embodiments, at least one chemical entity chosen from the compounds of Formula I is chosen from compounds of Formula Ib

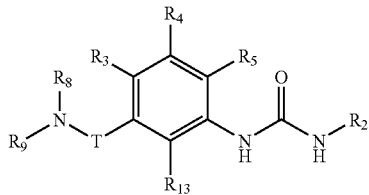

Formula Ib wherein
$R_8$ is lower alkyl; and
$R_9$ is optionally substituted alkyl, optionally substituted heterocycloalkyl, optionally substituted acyl or optionally substituted sulfonyl and
wherein $R_2$, $R_3$, $R_4$, $R_5$, $R_{13}$, and T are as described for compounds of Formula I.

In some embodiments, $R_9$ is —(CO)$OR_{10}$ wherein $R_{10}$ is hydrogen or lower alkyl.

In some embodiments, $R_9$ is —(SO$_2$)—$R_{17}$ wherein $R_{17}$ is lower alkyl or —$NR_{11}R_{12}$ wherein $R_{11}$ and $R_{12}$ are independently hydrogen or lower alkyl.

In some embodiments, $R_9$ is alkyl optionally substituted with optionally substituted amino.

In some embodiments, $R_9$ is optionally substituted heterocycloalkyl.

In some embodiments, $R_8$ is methyl or ethyl.

In some embodiments, at least one chemical entity chosen from the compounds of Formula I is chosen from compounds of Formula Ic

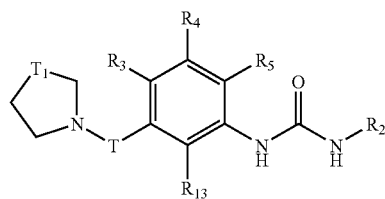

Formula Ic wherein
$T_1$ is —CHR$_{14}$—, —NR$_{14}$CHR$_{15}$—, —CHR$_{15}$NR$_{14}$—, or —CHR$_{14}$CHR$_{15}$—; and each $R_{14}$ and $R_{15}$ is independently selected from hydrogen, optionally substituted alkyl, optionally substituted acyl, carboxy, optionally substituted lower alkoxycarbonyl, optionally substituted aminocarbonyl, optionally substituted alkoxy, optionally substituted cycloalkoxy, optionally substituted sulfonyl, optionally substituted amino, optionally substituted cycloalkyl, and optionally substituted heterocycloalkyl and wherein $R_2$, $R_3$, $R_4$, $R_5$, $R_{13}$, and T are as described for compounds of Formula I.

In some embodiments, $R_{14}$ and $R_{15}$ are independently selected from hydrogen, methyl, carboxy, methoxycarbonyl, ethoxycarbonyl, propoxycarbonyl, isopropoxycarbonyl, tert-butoxycarbonyl, benzyloxycarbonyl, N,N-dimethylcarbamoyl, acetyl, methylacetyl, dimethylacetyl, propoxy, methoxy, cyclohexylmethyloxy, methylsulfonyl, ethylsulfonyl, n-propylsulfonyl, isopropylsulfonyl, azetidin-1-ylsulfonyl, N,N-dimethylaminosulfonyl, methanesulfonamido, N-methyl-methanesulfonamido, ethanesulfonamido, N-methyl-ethanesulfonamido, N-methoxycarbonyl-N-methylamino, N-ethoxycarbonyl-N-methylamino, N-isopropoxycarbonyl-N-methylamino, N-tert-butoxycarbonyl-N-methylamino, acetamido, N-methylacetamido, N-methylpropionamido, N-methylisobutyramido, amino, methylamino, dimethylamino, N-methyl-(N',N'-dimethylaminosulfonyl)amino, and piperidin-1-yl.

In some embodiments, at least one chemical entity chosen from the compounds of Formula I is chosen from compounds of Formula Id

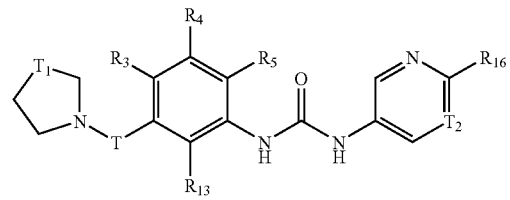

Formula Id wherein

T$_2$ is —C═ or —N═; and

R$_{16}$ is selected from hydrogen, halo, cyano, optionally substituted alkyl, optionally substituted alkoxy, and optionally substituted acyl and wherein R$_3$, R$_4$, R$_5$, R$_{13}$, and T are as described for compounds of Formula I and wherein T$_1$ is as described for compounds of Formula Ic.

In some embodiments, T$_2$ is —C═.

In some embodiments, T$_2$ is —N═.

In some embodiments, R$_{16}$ is selected from hydrogen, methyl, fluoro, cyano, methoxy, and acetyl.

In some embodiments, R$_{16}$ is hydrogen or methyl.

In some embodiments, at least one chemical entity is chosen from compounds of Formula I wherein:

W, X, Y and Z are —C═;

T is selected from —O—, —O-(lower alkylene)-, -(lower alkylene)-O—, —S—, —S-(lower alkylene)-, -(lower alkylene)-S—;

R$_1$ is an optionally substituted 5- to 7-membered nitrogen containing heterocycloalkyl which optionally includes an additional oxygen, nitrogen or sulfur in the heterocyclic ring; optionally substituted heterocycloalkyl; optionally substituted heteroaryl; or optionally substituted aryl;

R$_2$ is pyridin-3-yl which is optionally substituted with lower alkyl; phenyl which is optionally substituted with halo; optionally substituted pyrimidin-5-yl; or optionally substituted isoxazol-3-yl;

R$_3$ is hydrogen or fluoro;

R$_4$ is hydrogen, pyridinyl or fluoro;

R$_5$ is hydrogen or fluoro; and

R$_{13}$ is hydrogen or fluoro.

In some embodiments, at least one chemical entity is chosen from compounds of Formula I wherein:

W, X, Y and Z are —C═;

T is selected from —O—, —O-(lower alkylene)-, -(lower alkylene)-O—, —S—, —S-(lower alkylene)-, -(lower alkylene)-S—, R$_1$ is an optionally substituted 5- to 7-membered nitrogen containing heterocycloalkyl which optionally includes an additional oxygen, nitrogen or sulfur in the heterocyclic ring; optionally substituted heterocycloalkyl; optionally substituted heteroaryl; or optionally substituted aryl;

R$_2$ is pyridin-3-yl which is optionally substituted with lower alkyl; phenyl which is optionally substituted with halo; optionally substituted pyrimidin-5-yl; or optionally substituted isoxazol-3-yl;

R$_3$ is hydrogen or fluoro;

R$_4$ is hydrogen, pyridinyl or fluoro;

R$_5$ is hydrogen or fluoro; and

R$_{13}$ is hydrogen or fluoro, wherein one of R$_3$, R$_4$, and R$_5$ is not hydrogen.

In some embodiments, at least one chemical entity chosen from compounds of Formula I has one or more of the following: T is —O—; R$_1$ is tetrahydrofuranyl, tetrahydropyranyl, optionally substituted pyrrolidinyl, optionally substituted 3-oxo-tetrahydro-pyrrolo[1,2-c]oxazol-6-yl, optionally substituted morpholinyl, optionally substituted piperidinyl, optionally substituted pyridinyl or optionally substituted phenyl; and R$_4$ is pyridinyl or fluoro.

In some embodiments, R$_1$ is tetrahydrofuranyl, tetrahydropyranyl, substituted-pyrrolidinyl, 3-oxo-tetrahydro-pyrrolo[1,2-c]oxazol-6-yl, substituted-piperidinyl, pyridinyl or hydroxy-lower alkyl-phenyl; R$_3$ is hydrogen; and R$_4$ is fluoro.

In some embodiments, T is —O—.

In some embodiments, at least one chemical entity is chosen from compounds of Formula I wherein:

W, X, Y and Z are —C═;

T is selected from —O—, —O-(lower alkylene)-, -(lower alkylene)-O—, —S—, —S-(lower alkylene)-, -(lower alkylene)-S—;

R$_1$ is chosen from optionally substituted alkyl and optionally substituted heterocycloalkyl comprising an optionally substituted sulfuric diamide subunit;

R$_2$ is pyridin-3-yl which is optionally substituted with lower alkyl; phenyl which is optionally substituted with halo; optionally substituted pyrimidin-5-yl; or optionally substituted isoxazol-3-yl;

R$_3$ is hydrogen or fluoro;

R$_4$ is hydrogen, pyridinyl or fluoro;

R$_5$ is hydrogen or fluoro; and

R$_{13}$ is hydrogen or fluoro.

In some embodiments, at least one chemical entity is chosen from compounds of Formula I wherein:

W, X, Y and Z are —C═;

T is selected from —O—, —O-(lower alkylene)-, -(lower alkylene)-O—, —S—, —S-(lower alkylene)-, -(lower alkylene)-S—, R$_1$ is chosen from optionally substituted alkyl and optionally substituted heterocycloalkyl comprising an optionally substituted sulfuric diamide subunit;

R$_2$ is pyridin-3-yl which is optionally substituted with lower alkyl; phenyl which is optionally substituted with halo; optionally substituted pyrimidin-5-yl; or optionally substituted isoxazol-3-yl;

R$_3$ is hydrogen or fluoro;

R$_4$ is hydrogen, pyridinyl or fluoro;

R$_5$ is hydrogen or fluoro; and

R$_{13}$ is hydrogen or fluoro, wherein one of R$_3$, R$_4$, and R$_5$ is not hydrogen.

In some embodiments, at least one chemical entity chosen from compounds of Formula I has one or more of the following:

T is —O—;

R$_1$ is chosen from optionally substituted lower alkyl and 1,1-dioxo-1$\lambda^6$-[1,2,5]thiadiazolidinyl; 1,1-dioxo-1$\lambda^6$-[1,2,6]thiadiazinanyl; or 1,1-dioxo-1$\lambda^6$-2,3,3a,4,5,6-hexahydropyrrolo[1,2-b][1,2,5]thiadiazolyl, each of which is substituted with one or more lower alkyl groups; and R$_4$ is pyridinyl or fluoro.

In some embodiments,

R$_1$ is chosen from lower alkyl substituted with one or two groups chosen from optionally substituted alkoxy and optionally substituted amino; and 1,1-dioxo-1$\lambda^6$-[1,2,5]thiadiazolidinyl; 1,1-dioxo-1$\lambda^6$-[1,2,6]thiadiazinanyl; or 1,1-dioxo-1$\lambda^6$-2,3,3a,4,5,6-hexahydropyrrolo[1,2-b][1,2,5]thiadiazolyl, each of which is substituted with one or more methyl groups;

R$_3$ is hydrogen; and

R$_4$ is fluoro.

In some embodiments,

R$_1$ is chosen from lower alkyl substituted with one or two groups chosen from alkylsulfonylamino, carboxamido, optionally substituted aminosulfonylamino, and alkoxycarbonylamino; and 1,1-dioxo-1$\lambda^6$-2,3,3a,4,5,6-hexahydropyrrolo[1,2-b][1,2,5]thiadiazolyl substituted with one or more methyl groups;

R$_3$ is hydrogen;

R$_4$ is fluoro, and

T is —O—.

In certain embodiments, the compound of Formula I is chosen from

N-[5-fluoro-3-(2-methoxy-isopropoxy)phenyl][(6-methoxy (3-pyridyl))amino]carboxamide;

N-[5-fluoro-3-(2-methoxy-isopropoxy)phenyl] (3-pyridylamino)carboxamide;
[(6-methoxy(3-pyridyl))amino]-N-[3-(methylethoxy)phenyl]carboxamide;
N-[({5-fluoro-3-[(N-(3-pyridyl)carbamoyl)amino] phenoxy}methyl)cyclopentyl]acetamide;
N-(2-{5-fluoro-3-[(N-(3-pyridyl)carbamoyl)amino]phenoxy}-tert-butyl)acetamide;
N-{2-[5-fluoro-3-({N-[6-(trifluoromethyl)(3-pyridyl)]carbamoyl}amino)phenoxy]-tert-butyl}acetamide;
N-[2-(5-fluoro-3-{[N-(6-methoxy(3-pyridyl))carbamoyl]amino}phenoxy)-tert-butyl]acetamide;
N-({[3-fluoro-5-({[6-(trifluoromethyl)(3-pyridyl)]amino}carbonylamino)phenoxy]methyl}cyclopentyl)acetamide;
N-{[(3-fluoro-5-{[(6-methoxy(3-pyridyl))amino]carbonylamino}phenoxy)methyl]cyclopentyl}acetamide;
N-{5-fluoro-3-[2-(methoxycarbonylamino)ethoxy]phenyl}(3-pyridylamino)carboxamide;
N-(2-{3-fluoro-5-[(3-pyridylamino)carbonylamino]phenoxy}ethyl)acetamide;
N-[3-(2-{[(dimethylamino)sulfonyl]amino}ethoxy)-5-fluorophenyl] (3-pyridylamino)carboxamide;
N-(3-{2-[(ethylsulfonyl)amino]ethoxy}-5-fluorophenyl)(3-pyridylamino)carboxamide;
N-(2-{3-fluoro-5-[(3-pyridylamino)carbonylamino]phenoxy}ethyl)methoxy-N-methylcarboxamide;
N-(2-{3-fluoro-5-[(3-pyridylamino)carbonylamino]phenoxy}ethyl)-N-methylacetamide;
N-[3-(2-{[(dimethylamino)sulfonyl]methylamino}ethoxy)-5-fluorophenyl] (3-pyridylamino)carboxamide;
N-(3-{2-[(ethylsulfonyl)methylamino]ethoxy}-5-fluorophenyl)(3-pyridylamino)carboxamide;
N-[3-(2-{[(1Z)-1-(dimethylamino)-2-cyano-2-azavinyl]methylamino}ethoxy)-5-fluorophenyl] (3-pyridylamino)carboxamide;
N-[3-((1R)-2-{[(dimethylamino)sulfonyl]methylamino}-isopropoxy)-5-fluorophenyl] (3-pyridylamino)carboxamide;
N-(3-{(1R)-2-[(ethylsulfonyl)methylamino]-isopropoxy}-5-fluorophenyl)(3-pyridylamino)carboxamide;
N-(3-{(1R)-2-[(tert-butoxy)-N-methylcarbonylamino]-isopropoxy}-5-fluorophenyl)(3-pyridylamino)carboxamide;
N-{3-[(1R)-2-(methoxy-N-methylcarbonylamino)-isopropoxy]-5-fluorophenyl}(3-pyridylamino)carboxamide;
N-{3-[(1R)-1-methyl-2-(methylamino)ethoxy]-5-fluorophenyl}(3-pyridylamino)carboxamide;
N-[3-((1S)-2-{[(dimethylamino)sulfonyl]methylamino}-isopropoxy)-5-fluorophenyl] (3-pyridylamino)carboxamide;
N-(3-{(1S)-2-[(ethylsulfonyl)methylamino]-isopropoxy}-5-fluorophenyl)(3-pyridylamino)carboxamide;
N-((2S)-2-{3-fluoro-5-[(3-pyridylamino)carbonylamino]phenoxy}propyl)methoxy-N-methylcarboxamide;
N-((2S)-2-{3-fluoro-5-[(3-pyridylamino)carbonylamino]phenoxy}propyl)-N-methylacetamide;
N-[3-(2-{[(1E)-1-(dimethylamino)-2-cyano-2-azavinyl]methylamino}(1S)-isopropoxy)-5-fluorophenyl] (3-pyridylamino)carboxamide;
N-[3-((1S)-1-methyl-2-{methyl[(methylethyl)sulfonyl]amino}ethoxy)-5-fluorophenyl] (3-pyridylamino)carboxamide;
N-((2R)-2-{3-fluoro-5-[(3-pyridylamino)carbonylamino]phenoxy}propyl)-N-methylacetamide;
N-[3-(2-{[(1E)-1-(dimethylamino)-2-cyano-2-azavinyl]methylamino}(1R)-isopropoxy)-5-fluorophenyl] (3-pyridylamino)carboxamide;
N-[3-(2-{[(dimethylamino)sulfonyl]methylamino}ethoxy)-5-fluorophenyl][(6-methyl(3-pyridyl))amino]carboxamide;
N-(3-{2-[(ethylsulfonyl)methylamino]ethoxy}-5-fluorophenyl)[(6-methyl(3-pyridyl))amino]carboxamide;
N-[5-fluoro-3-(2-{methyl[(methylethyl)sulfonyl]amino}ethoxy)phenyl][(6-methyl(3-pyridyl))amino]carboxamide;
N-[3-(2-{[(dimethylamino)sulfonyl]methylamino}ethoxy)-5-fluorophenyl][(4-fluorophenyl)amino]carboxamide;
N-(3-{2-[(ethylsulfonyl)methylamino]ethoxy}-5-fluorophenyl)[(4-fluorophenyl)amino]carboxamide;
N-[5-fluoro-3-(2-{methyl[(methylethyl)sulfonyl]amino}ethoxy)phenyl][(4-fluorophenyl)amino]carboxamide;
N-(3-{(1R)-2-[(tert-butoxy)-N-methylcarbonylamino]-isopropoxy}-5-fluorophenyl) [(6-methyl(3-pyridyl))amino]carboxamide;
N-[3-((1R)-2-{[(dimethylamino)sulfonyl]methylamino}-isopropoxy)-5-fluorophenyl][(6-methyl(3-pyridyl))amino]carboxamide;
N-(3-{(1R)-2-[(ethylsulfonyl)methylamino]-isopropoxy}-5-fluorophenyl) [(6-methyl(3-pyridyl))amino]carboxamide;
N-[3-((1R)-1-methyl-2-{methyl[(methylethyl)sulfonyl]amino}ethoxy)-5-fluorophenyl][(6-methyl(3-pyridyl))amino]carboxamide;
N-{3-[(1R)-2-(methoxy-N-methylcarbonylamino)-isopropoxy]-5-fluorophenyl}[(6-methyl(3-pyridyl))amino]carboxamide;
N-[3-((1S)-2-{[(dimethylamino)sulfonyl]methylamino}-isopropoxy)-5-fluorophenyl][(6-methyl(3-pyridyl))amino]carboxamide;
N-(3-{(1S)-2-[(ethylsulfonyl)methylamino]-isopropoxy}-5-fluorophenyl)[(6-methyl(3-pyridyl))amino]carboxamide;
N-[3-((1S)-1-methyl-2-{methyl[(methylethyl)sulfonyl]amino}ethoxy)-5-fluorophenyl][(6-methyl(3-pyridyl))amino]carboxamide;
N-[(2S)-2-(3-fluoro-5-{[(6-methyl(3-pyridyl))amino]carbonylamino}phenoxy)propyl]methoxy-N-methylcarboxamide;
N-[(2S)-2-(3-fluoro-5-{[(6-methyl(3-pyridyl))amino]carbonylamino}phenoxy)propyl]-N-methylacetamide;
N-[3-(2-{[(1E)-1-(dimethylamino)-2-cyano-2-azavinyl]methylamino}(1S)-isopropoxy)-5-fluorophenyl][(6-methyl(3-pyridyl))amino]carboxamide;
N-{3-[2-{[(dimethylamino)sulfonyl]methylamino}-1-({[(dimethylamino)sulfonyl]methylamino}methyl)ethoxy]-5-fluorophenyl}(3-pyridylamino)carboxamide;
N-{3-[2-{[(dimethylamino)sulfonyl]methylamino}-1-({[(dimethylamino)sulfonyl]methylamino}methyl)ethoxy]-5-fluorophenyl}[(6-methyl(3-pyridyl))amino]carboxamide;
N-[3-((7aS,2R)-6-methyl-5,5-dioxo(2,3,6,7,7a-pentahydro-5-thia-6-azapyrrolizin-2-yloxy))-5-fluorophenyl] (3-pyridylamino)carboxamide;
N-[3-((2S,7aS)-6-methyl-5,5-dioxo(2,3,6,7,7a-pentahydro-5-thia-6-azapyrrolizin-2-yloxy))-5-fluorophenyl] (3-pyridylamino)carboxamide;
N-[3-((2R,7aR)-6-methyl-5,5-dioxo(2,3,6,7,7a-pentahydro-5-thia-6-azapyrrolizin-2-yloxy))-5-fluorophenyl] (3-pyridylamino)carboxamide;
N-[3-((7aS,2R)-6-methyl-5,5-dioxo(2,3,6,7,7a-pentahydro-5-thia-6-azapyrrolizin-2-yloxy))-5-fluorophenyl][(6-methyl(3-pyridyl))amino]carboxamide;

N-[3-((1S,7aR)-6-methyl-5,5-dioxo(2,3,6,7,7a-pentahydro-5-thia-6-azapyrrolizinyloxy))-5-fluorophenyl] (3-pyridylamino)carboxamide;

N-[3-((1S,7aR)-6-methyl-5,5-dioxo(2,3,6,7,7a-pentahydro-5-thia-6-azapyrrolizinyloxy))-5-fluorophenyl][(6-methyl(3-pyridyl))amino]carboxamide;

N-[3-((7aS,2R)-6-methyl-5,5-dioxo(2,3,6,7,7a-pentahydro-5-thia-6-azapyrrolizin-2-yloxy))-5-fluorophenyl][(4-fluorophenyl)amino]carboxamide;

N-{5-fluoro-3-[2-(5-methyl-1,1-dioxo(1,2,5-thiadiazolidin-2-yl))ethoxy]phenyl}(3-pyridylamino)carboxamide;

N-{5-fluoro-3-[2-(5-methyl-1,1-dioxo(1,2,5-thiadiazolidin-2-yl))ethoxy]phenyl}[(6-methyl(3-pyridyl))amino]carboxamide;

N-[3-(2,6-dimethyl-1,1-dioxo(1,2,6-thiadiazaperhydroin-4-yloxy))-5-fluorophenyl] (3-pyridylamino)carboxamide;

N-[3-(2,6-dimethyl-1,1-dioxo(1,2,6-thiadiazaperhydroin-4-yloxy))-5-fluorophenyl][(6-methyl(3-pyridyl))amino]carboxamide;

N-{3-[(2,5-dimethyl-1,1-dioxo(1,2,5-thiadiazolidin-3-yl))methoxy]-5-fluorophenyl}(3-pyridylamino)carboxamide;

N-{3-[(2,5-dimethyl-1,1-dioxo(1,2,5-thiadiazolidin-3-yl))methoxy]-5-fluorophenyl}[(6-methyl(3-pyridyl))amino]carboxamide;

N-[3-((2R,7aR)-6-methyl-5,5-dioxo(2,3,6,7,7a-pentahydro-5-thia-6-azapyrrolizin-2-yloxy))-5-fluorophenyl][(6-methyl(3-pyridyl))amino]carboxamide;

N-[3-((7aS,2R)-6-methyl-5,5-dioxo(2,3,6,7,7a-pentahydro-5-thia-6-azapyrrolizin-2-yloxy))-5-fluorophenyl]-N-hydroxy(3-pyridylamino)carboxamide; and N-[3-((7aS,2R)-6-methyl-5,5-dioxo(2,3,6,7,7a-pentahydro-5-thia-6-azapyrrolizin-2-yloxy))-5-fluorophenyl]-N-hydroxy[(6-methyl(3-pyridyl))amino]carboxamide.

In some embodiments, the present invention is related to a pharmaceutical composition comprising a pharmaceutically acceptable excipient or adjuvant and at least one chemical entity as described herein for Formula I.

The compounds of the present invention are selective for and modulate the cardiac sarcomere, and are useful to bind to and/or potentiate the activity of cardiac myosin, increasing the rate at which myosin hydrolyzes ATP. As used in this context, "modulate" means either increasing or decreasing myosin activity, whereas "potentiate" means to increase activity. It has also been determined in testing representative compounds of the invention, that their administration can also increase the contractile force in cardiac muscle fiber.

The compounds, pharmaceutical formulations and methods of the invention are used to treat heart disease, including but not limited to: acute (or decompensated) congestive heart failure, and chronic congestive heart failure; for example, diseases associated with systolic heart dysfunction. Additional therapeutic utilities include administration to stabilize heart function in patients awaiting a heart transplant, and to assist a stopped or slowed heart in resuming normal function following use of a bypass pump.

ATP hydrolysis is employed by myosin in the sarcomere to produce force. Therefore, an increase in ATP hydrolysis would correspond to an increase in the force or velocity of muscle contraction. In the presence of actin, myosin ATPase activity is stimulated >100 fold. Thus, ATP hydrolysis not only measures myosin enzymatic activity but also its interaction with the actin filament. A compound that modulates the cardiac sarcomere can be identified by an increase or decrease in the rate of ATP hydrolysis by myosin, for example exhibiting a 1.4 fold increase at concentrations less than 10 µM (for example, less than 1 µM). Preferred assays for such activity will employ myosin from a human source, although myosin from other organisms can also be used. Systems that model the regulatory role of calcium in myosin binding are also preferred.

Alternatively, a biochemically functional sarcomere preparation can be used to determine in vitro ATPase activity, for example, as described in U.S. Ser. No. 09/539,164, filed Mar. 29, 2000. The functional biochemical behavior of the sarcomere, including calcium sensitivity of ATPase hydrolysis, can be reconstituted by combining its purified individual components (including its regulatory components and myosin). Another functional preparation is the in vitro motility assay. It can be performed by adding test compound to a myosin-bound slide and observing the velocity of actin filaments sliding over the myosin covered glass surface (Kron S J. (1991) Methods Enzymol. 196:399-416).

The in vitro rate of ATP hydrolysis correlates to myosin potentiating activity, which can be determined by monitoring the production of either ADP or phosphate, for example as described in Ser. No. 09/314,464, filed May 18, 1999. ADP production can also be monitored by coupling the ADP production to NADH oxidation (using the enzymes pyruvate kinase and lactate dehydrogenase) and monitoring the NADH level either by absorbance or fluorescence (Greengard, P., *Nature* 178 (Part 4534): 632-634 (1956); *Mol Pharmacol* 1970 January; 6(1):31-40). Phosphate production can be monitored using purine nucleoside phosphorylase to couple phosphate production to the cleavage of a purine analog, which results in either a change in absorbance (*Proc Natl Acad Sci USA* 1992 Jun. 1; 89(11):4884-7) or fluorescence (*Biochem J* 1990 Mar. 1; 266(2):611-4). While a single measurement can be employed, it is preferred to take multiple measurements of the same sample at different times in order to determine the absolute rate of the protein activity; such measurements can have higher specificity in the presence of test compounds that have similar absorbance or fluorescence properties with those of the enzymatic readout.

Test compounds can be assayed in a highly parallel fashion using multiwell plates by placing the compounds either individually in wells or testing them in mixtures. Assay components including the target protein complex, coupling enzymes and substrates, and ATP can then be added to the wells and the absorbance or fluorescence of each well of the plate can be measured with a plate reader.

A preferred method uses a 384 well plate format and a 25 µL reaction volume. A pyruvate kinase/lactate dehydrogenase coupled enzyme system (Huang T G and Hackney D D. (1994) J Biol Chem 269(23):16493-16501) is used to measure the rate of ATP hydrolysis in each well. As will be appreciated by those in the art, the assay components are added in buffers and reagents. Since the methods outlined herein allow kinetic measurements, incubation periods are optimized to give adequate detection signals over the background. The assay is done in real time giving the kinetics of ATP hydrolysis, which increases the signal to noise ratio of the assay.

Modulation of cardiac muscle fiber contractile force can be measured using detergent permeabilized cardiac fibers (also referred to as skinned cardiac fibers), for example, as described by Haikala H, et al (1995) J Cardiovasc Pharmacol 25(5):794-801. Skinned cardiac fibers retain their intrinsic sarcomeric organization, but do not retain all aspects of cellular calcium cycling, this model offers two advantages: first, the cellular membrane is not a barrier to compound penetration, and second, calcium concentration is controlled. Therefore, any increase in contractile force is a direct measure of the test compound's effect on sarcomeric proteins. Tension measurements are made by mounting one end of the muscle fiber to a stationary post and the other end to a transducer that can measure force. After stretching the fiber to remove slack, the force transducer records increased tension as the fiber begins to contract. This measurement is called the isometric tension, since the fiber is not allowed to shorten. Activation of the permeabilized muscle fiber is accomplished by placing it in a buffered calcium solution, followed by addition of test compound or control. When tested in this manner, compounds of the invention caused an increase in force at calcium concentrations associated with physiologic contractile activity, but very little augmentation of force in relaxing buffer at low calcium concentrations or in the absence of calcium (the EGTA data point).

Selectivity for the cardiac sarcomere and cardiac myosin can be determined by substituting non-cardiac sarcomere components and myosin in one or more of the above-described assays and comparing the results obtained against those obtained using the cardiac equivalents.

A compound's ability to increase observed ATPase rate in an in vitro reconstituted sarcomere assay could result from the increased turnover rate of S1-myosin or, alternatively, increased sensitivity of a decorated actin filament to $Ca^{++}$-activation. To distinguish between these two possible modes of action, the effect of the compound on ATPase activity of S1 with undecorated actin filaments is initially measured. If an increase of activity is observed, the compound's effect on the Ca-responsive regulatory apparatus could be disproved. A second, more sensitive assay, can be employed to identify compounds whose activating effect on S1-myosin is enhanced in the presence of a decorated actin (compared to pure actin filaments). In this second assay activities of cardiac-S1 and skeletal-S1 on cardiac and skeletal regulated actin filaments (in all 4 permutations) are compared. A compound that displays its effect on cardiac-S1/cardiac actin and cardiac-S1/skeletal actin, but not on skeletal-S1/skeletal actin and skeletal-S1/cardiac actin systems, can be confidently classified as cardiac-S1 activator.

Initial evaluation of in vivo activity can be determined in cellular models of myocyte contractility, e.g., as described by Popping S, et al ((1996) Am. J. Physiol. 271: H357-H364) and Wolska B M, et al ((1996) Am. J. Physiol. 39:H24-H32). One advantage of the myocyte model is that the component systems that result in changes in contractility can be isolated and the major site(s) of action determined. Compounds with cellular activity (for example, selecting compounds having the following profile: >120% increase in fractional shortening over basal at 2 µM, limited changes in diastolic length (<5% change), and no significant decrease in contraction or relaxation velocities) can then be assessed in whole organ models, such as such as the Isolated Heart (Langendorff) model of cardiac function, in vivo using echocardiography or invasive hemodynamic measures, and in animal-based heart failure models, such as the Rat Left Coronary Artery Occlusion model. Ultimately, activity for treating heart disease is demonstrated in blinded, placebo-controlled, human clinical trials.

At least one chemical entity having the structure of Formula I are administered at a therapeutically effective dosage, e.g., a dosage sufficient to provide treatment for the disease states previously described. While human dosage levels have yet to be optimized for the compounds of the invention, generally, a daily dose is from about 0.05 to 100 mg/kg of body weight, for example about 0.10 to 10.0 mg/kg of body weight, or, for example, about 0.15 to 1.0 mg/kg of body weight. Thus, for administration to a 70 kg person, the dosage range would be about 3.5 to 7000 mg per day, for example, about 7.0 to 700.0 mg per day, or for example, about 10.0 to 100.0 mg per day. The amount of active compound administered will, of course, be dependent on the subject and disease state being treated, the severity of the affliction, the manner and schedule of administration and the judgment of the prescribing physician; for example, a likely dose range for oral administration would be about 70 to 700 mg per day, whereas for intravenous administration a likely dose range would be about 700 to 7000 mg per day, the active agents being selected for longer or shorter plasma half-lives, respectively.

Administration of the compounds of the invention or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administration are customary in treating the indications that are the subject of the present invention.

Pharmaceutically acceptable compositions include solid, semi-solid, liquid and aerosol dosage forms, such as, e.g., tablets, capsules, powders, liquids, suspensions, suppositories, aerosols or the like. The compounds can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The compounds can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical formulation will contain about 0.005% to 95%, or about 0.5% to 50% by weight of a compound of the invention. Actual methods of preparing such dosage forms are known, or will be apparent, to those skilled in this art; for example, see *Remington's Pharmaceutical Sciences*, Mack Publishing Company, Easton, Pa.

In addition, the compounds of the invention can be co-administered with, and the pharmaceutical compositions can include, other medicinal agents, pharmaceutical agents, adjuvants, and the like. Suitable additional active agents include, for example: therapies that retard the progression of heart failure by down-regulating neurohormonal stimulation of the heart and attempt to prevent cardiac remodeling (e.g., ACE inhibitors or β-blockers); therapies that improve cardiac function by stimulating cardiac contractility (e.g., positive inotropic agents, such as the β-adrenergic agonist dobutamine or the phosphodiesterase inhibitor milrinone); and therapies that reduce cardiac preload (e.g., diuretics, such as furosemide).

In one preferred embodiment, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid that will be subsequently diluted to the above percentages. In certain embodiments, the composition will comprise 0.2-2% of the active agent in solution.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example, less than 10 microns.

Generally, to employ the compounds of the invention in a method of screening for myosin binding, myosin is bound to a support and a compound of the invention is added to the assay. Alternatively, the compound of the invention can be bound to the support and the myosin added. Classes of compounds among which novel binding agents may be sought include specific antibodies, non-natural binding agents identified in screens of chemical libraries, peptide analogs, etc. Of interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like. See, e.g., U.S. Pat. No. 6,495,337, incorporated herein by reference.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

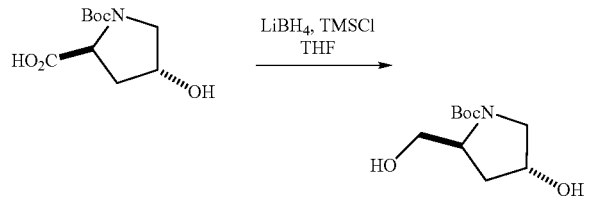

(2S,4R)-tert-butyl 4-hydroxy-2-(hydroxymethyl)pyrrolidine-1-carboxylate. To a 0° C. suspension of LiBH$_4$ (2.0 equiv) in THF (0.67 M) was slowly added TMSCl (4.0 equiv) by syringe. After stirring at room temperature for 30 minutes, (2S,4R)-1-(tert-butoxycarbonyl)-4-hydroxypyrrolidine-2-carboxylic acid (1.0 equiv) was then added, and the resulting mixture was stirred at room temperature overnight. The reaction was quenched by the careful addition of sat'd. aq. NaHCO$_3$, and the mixture was diluted with EtOAc, and the organice layer was washed twice with sat'd. aq. NaHCO$_3$, once with brine, dried over anhydrous sodium sulfate, filtered, and concentrated in vacuo. The title compound was isolated in 65% yield and used without further purification.

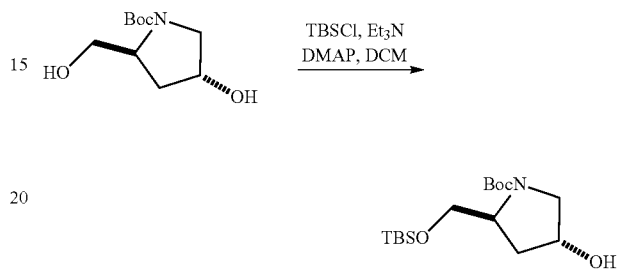

(2S,4R)-tert-butyl 2-((tert-butyldimethylsilyloxy)methyl)-4-hydroxypyrrolidine-1-carboxylate. To a 0° C. solution of (2S,4R)-tert-butyl 4-hydroxy-2-(hydroxymethyl)pyrrolidine-1-carboxylate (1.0 equiv) and Et$_3$N (1.05 equiv) in dichloromethane (0.5 M) was added TBSCl (1.05 equiv), followed by a few crystals of DMAP. The solution was allowed to warm to room temperature and stirred overnight. The reaction mixture was then diluted with dichloromethane, and washed with sat'd. aq. NaHCO$_3$. The organic layer was dried over anhydrous sodium sulfate, filtered and concentrated in vacuo to provide the title compound (95%), which was used without further purification.

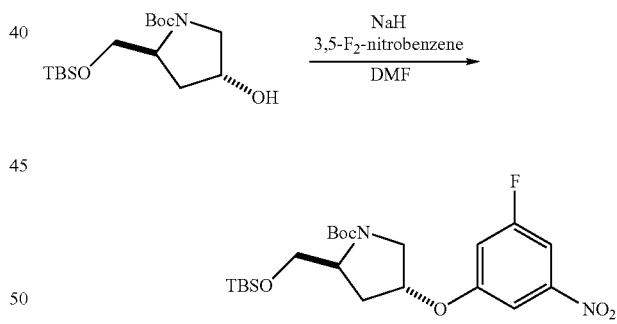

(2S,4R)-tert-butyl 2-((tert-butyldimethylsilyloxy)methyl)-4-(3-fluoro-5-nitrophenoxy)pyrrolidine-1-carboxylate. To a 0° C. solution of (2S,4R)-tert-butyl 2-((tert-butyldimethylsilyloxy)methyl)-4-hydroxypyrrolidine-1-carboxylate (1 equiv) in DMF (0.5 M) was added NaH (1.3 equiv) as a solid. After stirring for 30 minutes at 0° C., 3,5-difluoronitrobenzene (1.2 equiv) was added by syringe. The reaction mixture was allowed to warm to room temperature and stirred overnight. The reaction was quenched by the addition of water, and the mixture was diluted with EtOAc. The organic layer was washed four times with water and once with brine, dried over anhydrous sodium sulfate, filtered and concentrated in vacuo. Purification by flash chromatography (10-20% EtOAc/Hexanes) provided the title compound in 66% yield.

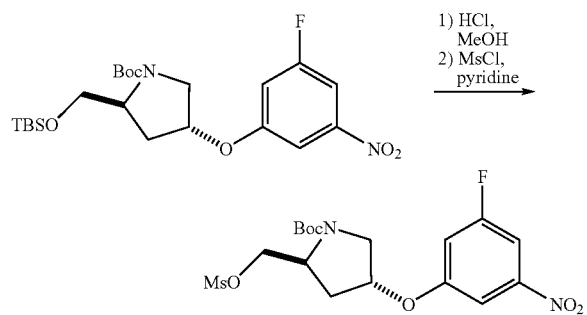

(2S,4R)-tert-butyl 4-(3-fluoro-5-nitrophenoxy)-2-((methylsulfonyloxy)methyl)pyrrolidine-1-carboxylate. To a solution of (2S,4R)-tert-butyl 2-((tert-butyldimethylsilyloxy)methyl)-4-(3-fluoro-5-nitrophenoxy)pyrrolidine-1-carboxylate (1.0 equiv) in MeOH (0.2 M) was added aq. HCl, (1N, 0.04 equiv). After 1 h, reaction was complete as judged by TLC (40% EtoAc/Hexanes). The reaction was quenched by the addition of solid NaHCO₃ (10 equiv), and the mixture was stirred until it was alkaline as judged by pH paper. The mixture was filtered through a pad of celite and concentrated in vacuo. The oil was dissolved in EtOAc and washed with sat. aq. NaHCO₃ and brine. The organic layer was dried over anhydrous sodium sulfate, filtered and concentrated in vacuo to provide the desired primary alcohol, which was used without further purification. The alcohol (1 equiv) was dissolved in THF (0.1 M), and Et₃N (1.1 equiv) was added. After the solution was cooled to 0° C., MsCl (1.05 equiv) was added dropwise by syringe. The reaction was then allowed to warm to room temperature and was judged complete by TLC (EtOAc) after 30 minutes. The reaction mixture was diluted with EtOAc (20 volume equivalents) and washed with sat'd. aq. NaHCO₃ (10 volume equivalents) and brine (10 volume equivalents). The organic layer was dried over anhydrous sodium sulfate, filtered and concentrated in vacuo to provide the title compound as a yellow oil in quantitative yield.

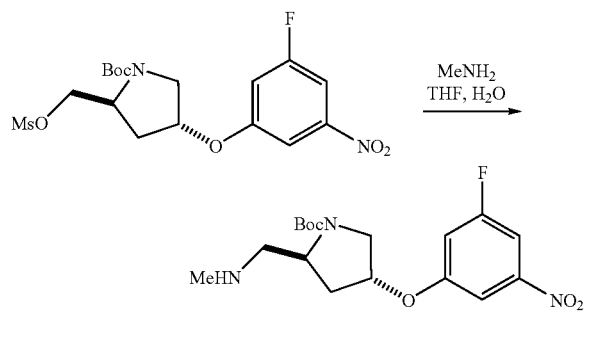

(2S,4R)-tert-butyl 4-(3-fluoro-5-nitrophenoxy)-2-((methylamino)methyl)pyrrolidine-1-carboxylate. To a solution of (2S,4R)-tert-butyl 4-(3-fluoro-5-nitrophenoxy)-2-((methylsulfonyloxy)methyl)pyrrolidine-1-carboxylate (1.0 equiv) in THF (0.4 M) was added 40% aq. methylamine (90 equiv). The resulting solution was heated to 55° C. overnight. The reaction mixture was cooled to room temperature and diluted with EtOAc (20 volume equivalents) and washed twice with sat. aq. NaHCO₃ (10 volume equivalents) and once with brine (10 volume equivalents). The organic layer was dried over anhydrous sodium sulfate, filtered and concentrated in vacuo to provide the title compound as a dark oil with 119% mass balance; the material was used without further purification.

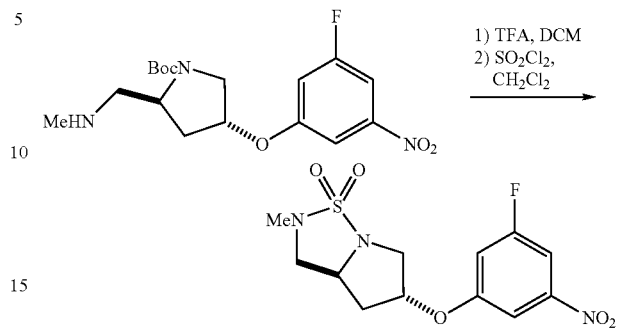

(3aS,5R)-5-(3-fluoro-5-nitrophenoxy)-2-methylhexahydropyrrolo[1,2-b][1,2,5]-1,1-dioxythiadiazole. To a solution of (2S,4R)-tert-butyl 4-(3-fluoro-5-nitrophenoxy)-2-((methylamino)methyl)pyrrolidine-1-carboxylate (1.0 equiv) in dichloromethane (0.5 M) was added trifluoroacetic acid (2 volume equivalents), and the mixture was stirred for 1 h. The mixture was concentrated in vacuo, and the residue was dissolved in EtOAc (5 volume equivalents) and 2 N NaOH (15 volume equivalents). The organic layer was separated and the aqueous layer was extracted with EtOAc (15 volume equivalents). The combined organic layers were washed with brine (10 volume equivalents), dried over anhydrous sodium sulfate, filtered and concentrated in vacuo to provide the desired diamine, which was immediately carried into the next reaction. To a cooled (−10° C.) solution of the diamine (1 equiv) in dichloromethane (0.1 M) was added sulfuryl chloride (1.0 M in DCM, 1.05 equiv) dropwise while maintaining the reaction temperature below 0° C. Diisopropylethylamine (2.20 equiv) was then added dropwise, and the reaction was allowed to warm to room temperature. The reaction was quenched with sat. aq. NaHCO₃ (10 volume equivalents), and the layers were separated. The organic layer was dried over anhydrous sodium sulfate, filtered, and concentrated in vacuo. The residue was passed through a plug of silica gel, eluting with EtOAc, to provide the title compound in 35% yield.

3-fluoro-5-((3aS,5R)-2-methylhexahydropyrrolo[1,2-b][1,2,5]thiadiazol-5-yloxy)aniline. A suspension of (3aS,5R)-5-(3-fluoro-5-nitrophenoxy)-2-methylhexahydropyrrolo[1,2-b][1,2,5]-1,1-dioxythiadiazole (1.0 equiv) and 10% Pd/C in MeOH (0.2 M) was placed in a Parr bomb and pressurized with hydrogen gas (60 psi). After 3 h, the reaction mixture was vented to the atmosphere and filtered through a pad of celite; the celite pad was rinsed with MeOH, and the resulting solution was concentrated in vacuo to provide the title compound in quantitative yield.

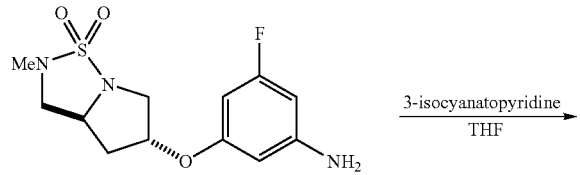

1-(3-fluoro-5-((3aS,5R)-2-methylhexahydropyrrolo[1,2-b][1,2,5]-1,1-dioxythiadiazol-5-yloxy)phenyl)-3-(pyridin-3-yl)urea. To a room-temperature solution of 3-fluoro-5-((3aS,5R)-2-methylhexahydropyrrolo[1,2-b][1,2,5]thiadiazol-5-yloxy)aniline (1 equiv) in THF (0.2 M) was added 3-isocyanatopyridine (1.1 equiv) as a solid. The reaction was allowed to stir overnight, after which the reaction was judged to be complete by HPLC/MS. The solution was diluted with EtOAc, washed with sat. aq. NaHCO$_3$ and brine. The organic layer was dried over anhydrous sodium sulfate, filtered and concentrated in vacuo. Flash chromatography (7.5% MeOH/DCM) provided the title compound (68%). m/z=422.1 (M+H).

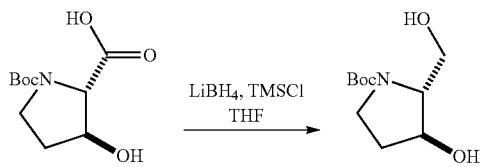

(2R,3S)-tert-butyl 3-hydroxy-2-(hydroxymethyl)pyrrolidine-1-carboxylate. To a 0° C. suspension of LiBH$_4$ (2.0 equiv) in THF (0.5 M) was slowly added TMSCl (4.0 equiv) by syringe. After stirring at room temperature for 30 minutes, (2S,3S)-1-(tert-butoxycarbonyl)-3-hydroxypyrrolidine-2-carboxylic acid (1.0 equiv) was then added, and the resulting mixture was stirred at room temperature overnight. The reaction was quenched by the careful addition of sat'd. aq. NaHCO$_3$, and the mixture was diluted with EtOAc, and the organic layer was washed twice with sat'd. aq. NaHCO$_3$, once with brine, dried over anhydrous sodium sulfate, filtered, and concentrated in vacuo. The title compound was isolated in 55% yield and used without further purification.

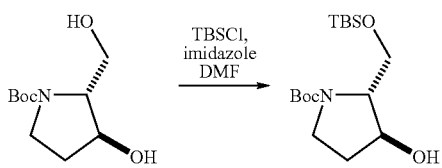

(2R,3S)-tert-butyl 2-((tert-butyldimethylsilyloxy)methyl)-3-hydroxypyrrolidine-1-carboxylate. To a 0° C. solution of (2R,3S)-tert-butyl 3-hydroxy-2-(hydroxymethyl)pyrrolidine-1-carboxylate (1.0 equiv) and Et$_3$N (1.05 equiv) in dichloromethane (0.5 M) was added TBSCl (1.05 equiv), followed by a few crystals of DMAP. The solution was allowed to warm to room temperature and stirred overnight. The reaction mixture was then diluted with dichloromethane, and washed with sat'd. aq. NaHCO$_3$. The organic layer was dried over anhydrous sodium sulfate, filtered and concentrated in vacuo to provide the title compound (99%), which was used without further purification.

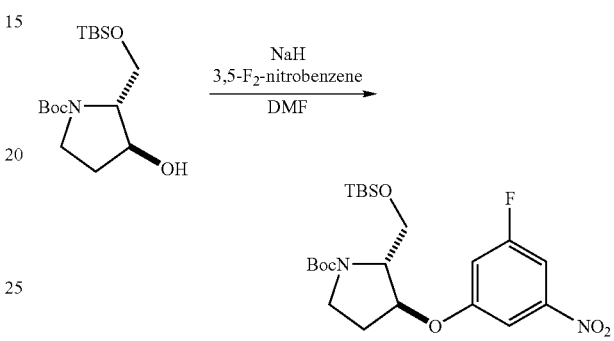

(2R,3S)-tert-butyl 2-((tert-butyldimethylsilyloxy)methyl)-3-(3-fluoro-5-nitrophenoxy)pyrrolidine-1-carboxylate. To a 0° C. solution of (2R,3S)-tert-butyl 2-((tert-butyldimethylsilyloxy)methyl)-3-hydroxypyrrolidine-1-carboxylate (1 equiv) in DMF (0.5 M) was added NaH (1.3 equiv) as a solid. After stirring for 15 min at 0° C., 3,5-difluoronitrobenzene (1.2 equiv) was added by syringe. The reaction mixture was allowed to warm to room temperature and stirred for 2 h. The reaction was quenched by the addition of water, and the mixture was diluted with EtOAc. The organic layer was washed four times with water and once with brine, dried over anhydrous sodium sulfate, filtered and concentrated in vacuo. Purification by flash chromatography (0-20% EtOAc/Hexanes) provided the title compound in 82% yield.

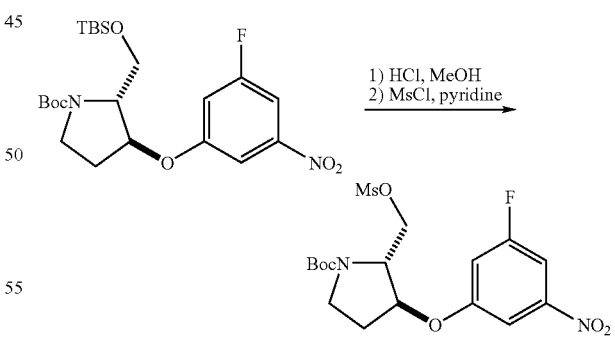

(2R,3S)-tert-butyl 3-(3-fluoro-5-nitrophenoxy)-2-((methylsulfonyloxy)methyl)pyrrolidine-1-carboxylate. To a solution of (2R,3S)-tert-butyl 2-((tert-butyldimethylsilyloxy)methyl)-3-(3-fluoro-5-nitrophenoxy)pyrrolidine-1-carboxylate (1.0 equiv) in MeOH (0.2 M) was added aq. HCl, (1N, 0.04 equiv). The reaction was quenched by the addition of solid NaHCO$_3$ (10 equiv), and the mixture was stirred until it was alkaline as judged by pH paper. The mixture was filtered through a pad of celite and concentrated in vacuo. The oil was dissolved in EtOAc and washed with sat. aq. NaHCO₃ and brine. The organic layer was dried over anhydrous sodium sulfate, filtered and concentrated in vacuo to provide the desired primary alcohol, which was used without further purification. The alcohol (1 equiv) was dissolved in pyridine (0.2 M). After the solution was cooled to 0° C., MsCl (2.0 equiv) was added dropwise by syringe. The reaction was then allowed to warm to room temperature and was judged complete by LCMS after 1 h. The reaction mixture was diluted with EtOAc and washed with sat'd. aq. NaHCO₃ and brine. The organic layer was dried over anhydrous sodium sulfate, filtered and concentrated in vacuo to provide the title compound as an oil in 94% yield.

The combined organic layers were washed with brine, dried over anhydrous sodium sulfate, filtered and concentrated in vacuo to provide the desired diamine, which was immediately carried into the next reaction. To a cooled (−10° C.) solution of the diamine (1 equiv) in dichloromethane (0.1 M) was added sulfuryl chloride (1.0 M in DCM, 1.05 equiv) dropwise while maintaining the reaction temperature below 0° C. Diisopropylethylamine (2.20 equiv) was then added dropwise, and the reaction was allowed to warm to room temperature. The reaction was quenched with sat. aq. NaHCO₃ and the layers were separated. The organic layer was dried over anhydrous sodium sulfate, filtered, and concentrated in vacuo. The residue was passed through a plug of silica gel, eluting with EtOAc, to provide the title compound in 21% yield.

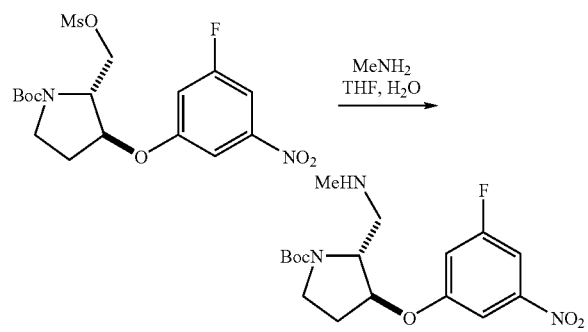

(2R,3S)-tert-butyl 3-(3-fluoro-5-nitrophenoxy)-2-((methylamino)methyl)pyrrolidine-1-carboxylate. To a solution of (2R,3S)-tert-butyl 3-(3-fluoro-5-nitrophenoxy)-2-((methylsulfonyloxy)methyl)pyrrolidine-1-carboxylate (1.0 equiv) in THF (0.4 M) was added 40% aq. methylamine (90 equiv). The resulting solution was heated to 55° C. overnight. The reaction mixture was cooled to room temperature and diluted with EtOAc (20 volume equivalents) and washed twice with sat. aq. NaHCO₃ and once with brine. The organic layer was dried over anhydrous sodium sulfate, filtered and concentrated in vacuo to provide the title compound as a dark oil with 147% mass balance; the material was used without further purification.

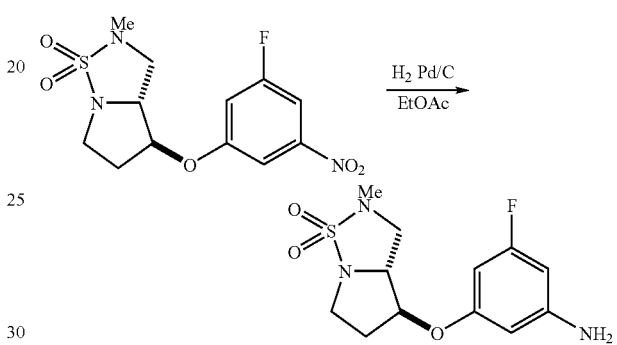

3-fluoro-5-((3aR,4S)-2-methylhexahydropyrrolo[1,2-b][1,2,5]-1,1-dioxythiadiazol-4-yloxy)aniline. A suspension of (3aR,4S)-4-(3-fluoro-5-nitrophenoxy)-2-methylhexahydropyrrolo[1,2-b][1,2,5]-1,1-dioxythiadiazole (1.0 equiv) and 10% Pd/C in EtOAc (0.2 M) was placed in a Parr bomb and pressurized with hydrogen gas (50 psi). After 3 h, the reaction mixture was vented to the atmosphere and filtered through a pad of celite; the celite pad was rinsed with EtOAc, and the resulting solution was concentrated in vacuo to provide the title compound in quantitative yield.

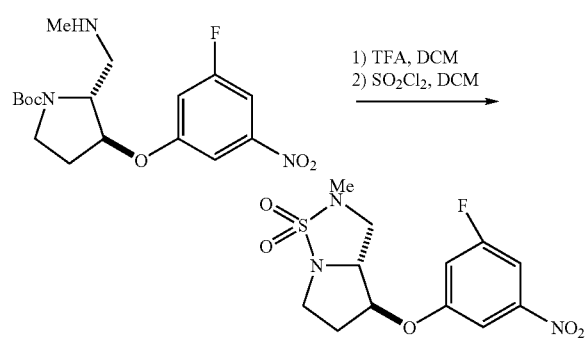

(3aR,4S)-4-(3-fluoro-5-nitrophenoxy)-2-methylhexahydropyrrolo[1,2-b][1,2,5]-1,1-dioxythiadiazole. To a solution of (2R,3S)-tert-butyl 3-(3-fluoro-5-nitrophenoxy)-2-((methylamino)methyl)pyrrolidine-1-carboxylate (1.0 equiv) in dichloromethane (0.5 M) was added trifluoroacetic acid (2 volume equivalents), and the mixture was stirred for 1 h. The mixture was concentrated in vacuo, and the residue was dissolved in EtOAc and 2 N NaOH. The organic layer was separated and the aqueous layer was extracted with EtOAc.

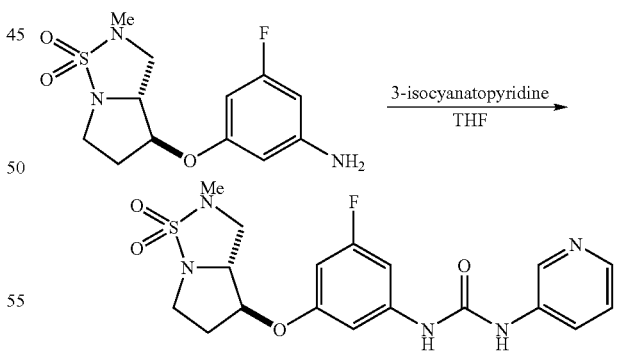

1-(3-fluoro-5-((3aR,4S)-2-methylhexahydropyrrolo[1,2-b][1,2,5]thiadiazol-4-yloxy)phenyl)-3-(pyridin-3-yl)urea.
To a room-temperature solution of 3-fluoro-5-((3aR,4S)-2-methylhexahydropyrrolo[1,2-b][1,2,5]-1,1-dioxythiadiazol-4-yloxy)aniline (1 equiv) in THF (0.2 M) was added 3-isocyanatopyridine (1.1 equiv) as a solid. The reaction was allowed to stir overnight. The solution was diluted with EtOAc, washed with sat. aq. NaHCO₃ and brine. The organic layer was dried over anhydrous sodium sulfate, filtered and concentrated in vacuo. Flash chromatography (5% MeOH/DCM) provided the title compound (60%). m/z=422.1 (M+H).

Example 2

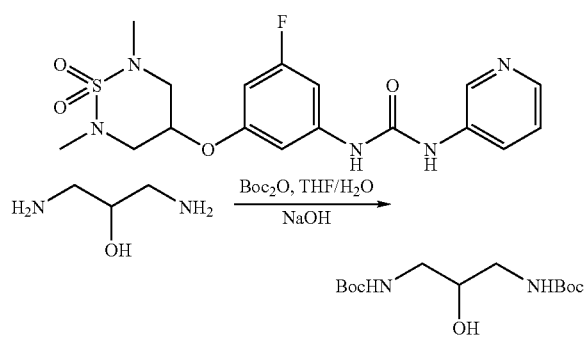

To 13.5 g (0.15 mol) of 1,3-diaminopropan-2-ol and 14.4 g (0.36 mol) of NaOH in 400 ml THF and 200 ml H$_2$O at 0° C. was added 72 g (0.33 mol) of Boc$_2$O in portions. The reaction mixture was warmed up to RT and stirred overnight. To this mixture was added 300 ml of EtOAc. The layers were separated and the aqueous layer was extracted with 200 ml EtOAc. The combined organic layer was dried with MgSO$_4$ and concentrated to give di-tert-butyl 2-hydroxypropane-1,3-diyldicarbamate in quantitative yield.

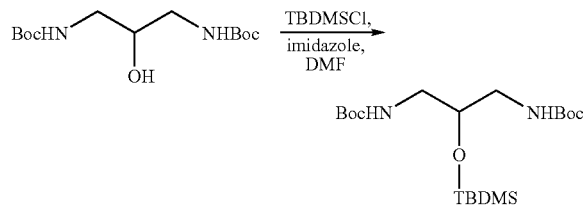

To 29.0 g (0.1 mol) of di-tert-butyl 2-hydroxypropane-1,3-diyldicarbamate and 17.0 g (0.25 mol) of imidazole in 200 ml DMF at 0° C., was added 18.09 g (0.12 mol) of t-butyldimethylsilylchloride (TBDSMCl) in portions. The reaction was warmed up to RT and stirred for 2 hours. To this mixture was added 400 ml ether and 400 ml brine. The layers were separated and the aqueous layer was extracted with 400 ml ether. The combined organic layer was dried and concentrated to give 35 g of di-tert-butyl 2-(tert-butyldimethylsilyloxy)propane-1,3-diyldicarbamate (86% yield).

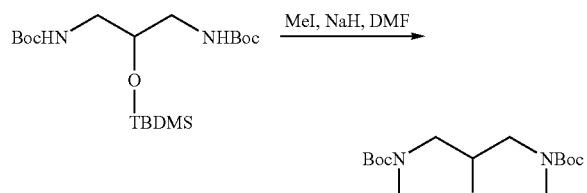

To 20.2 g (50 mmol) of di-tert-butyl 2-(tert-butyldimethylsilyloxy)propane-1,3-diyldicarbamate in 300 ml DMF under N$_2$ at 0° C., was added 4.8 g (0.12 mol) of sodium hydride in portions. The mixture was stirred for 30 min at 0° C. Methyl iodide (17.0 g, 0.12 mol) was added dropwise. The reaction was stirred for 2 hours. To the reaction mixture was added 500 ml brine and 500 ml ether. The layers were separated and the aqueous layer was extracted with 300 ml ether. The combined organic layer was dried with MgSO$_4$ and concentrated to give 21 g of di-tert-butyl 2-(tert-butyldimethylsilyloxy)propane-1,3-diylbis(methylcarbamate) (98%).

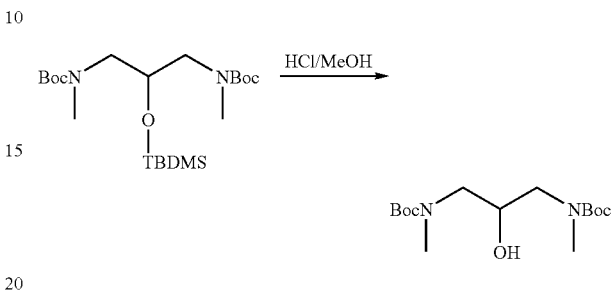

Di-tert-butyl 2-(tert-butyldimethylsilyloxy)propane-1,3-diylbis (methylcarbamate) (21 g, 48.6 mmol) was dissolved into 200 ml methanol at 0° C. Concentrated HCl (4 mL) was added dropwise and the reaction mixture was stirred at RT for 6 hrs. The mixture was placed over an ice water bath and 10 g of NaHCO$_3$ was added slowly. Then the reaction mixture was dried with MgSO$_4$, and then filtered. The filtrate was concentrated to yield 15.0 g of di-tert-butyl 2-hydroxypropane-1,3-diylbis(methylcarbamate) (97%).

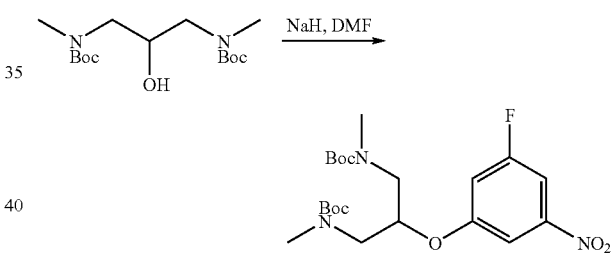

To 15.0 g (47.1 mmol) of di-tert-butyl 2-hydroxypropane-1,3-diylbis(methylcarbamate) and 11.9 g (75 mmol) of 1-nitro-3,5-difluorobenzene in 100 ml DMF under N$_2$ at 0° C. was added 2.4 g (60 mmol) of NaH in portions. The resultant mixture was stirred at 0° C. for 30 min after which approximately 1 mL of H$_2$O was added slowly. The reaction mixture was diluted with 200 mL EtOAc and 200 mL saturated NH$_4$Cl. The layers were separated and the organic layer was washed with 200 mL of saturated NH$_4$Cl. The organic layer was dried and concentrated. Then the residue was purified by column chromatography over silica gel (EtOAc:Hex=1:6) to give 10.3 g (45%) of di-tert-butyl 2-(3-fluoro-5-nitrophenoxy)propane-1,3-diylbis(methylcarbamate).

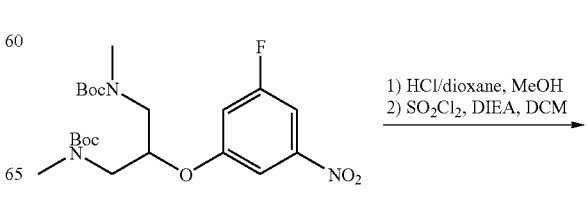

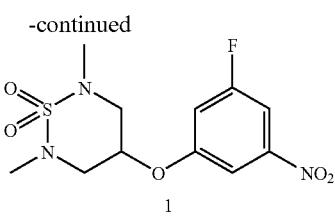

1

To a solution of 4.6 g (10 mmol) di-tert-butyl 2-(3-fluoro-5-nitrophenoxy)propane-1,3-diylbis(methylcarbamate) in 5 mL MeOH was added 10 ml 4N HCl/dioxane slowly. The reaction mixture was stirred at RT for 1 hour. The reaction mixture was concentrated to a residue. To 1.65 g of the resultant residue in 20 ml DCM at 0° C., was added 6.95 ml (40 mmol) of diisopropylethyl amine (DIEA) followed by the dropwise addition of 1.35 g (10 mmol) of $SO_2Cl_2$. The reaction mixture was stirred at overnight at RT. The solvents were removed and the resultant residue was purified by reverse phase HPLC (30% AcCN: water, over 45 min) to yield 1 (56%).

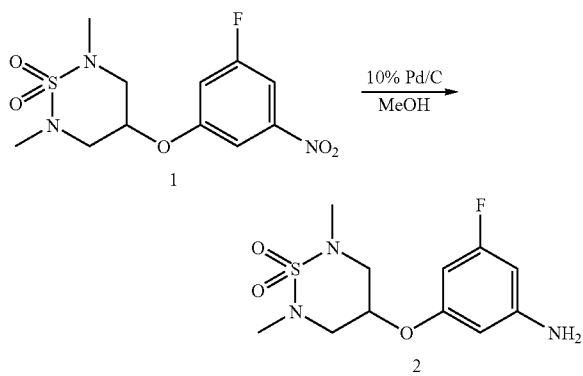

To compound 1 (0.89 g, 2.8 mmol) in 50 ml MeOH was added 0.25 g of 10% Pd/C. The mixture was stirred in Parr bomb at 45 psi hydrogen atmosphere for 1 hour. The reaction mixture was filtered through celite. The filtrate was concentrated to give 0.7 g of the aniline 2 (86% yield).

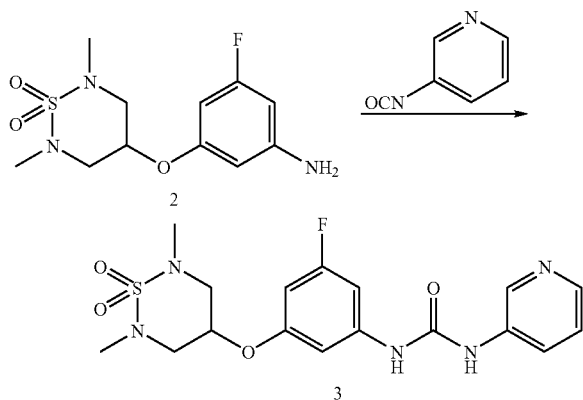

To 145 mg (0.5 mmol) of 2 in 2 ml DCM and 1 ml DMF was added 60 mg (0.5 mmol) of 3-isocyanatopyridine. The reaction mixture was stirred for 10 minute. DCM was removed. 0.7 ml MeOH was added to the reaction mixture. The desired final compound precipitated out and it was filtered to give 100 mg of the target compound 3 (50% yield). LC-MS: (M+) 410.1.

Example 3

Target Identification Assays

Specificity assays: Specificity towards cardiac myosin is evaluated by comparing the effect of the chemical entity on actin-stimulated ATPase of a panel of myosin isoforms: cardiac, skeletal and smooth muscle, at a single 50 μM concentration or to multiple concentrations of the chemical entity.

Myofibril assays: To evaluate the effect of compounds on the ATPase activity of full-length cardiac myosin in the context of native sarcomere, skinned myofibril assays are performed. Rat cardiac myofibrils are obtained by homogenizing rat cardiac tissue in the presence of detergent. Such treatment removes membranes and majority of soluble cytoplasmic proteins but leaves intact cardiac sarcomeric acto-myosin apparatus. Myofibril preparations retain the ability to hydrolyze ATP in an $Ca^{++}$ controlled manner. ATPase activities of such myofibril preparations in the presence and absence of compounds are assayed at $Ca^{++}$ concentrations giving 50% and 100% of a maximal rate.

Example 4

In Vitro Model of Dose Dependent Cardiac Myosin ATPase Modulation

Dose responses are measured using a calcium-buffered, pyruvate kinase and lactate dehydrogenase-coupled ATPase assay containing the following reagents (concentrations expressed are final assay concentrations): Potassium PIPES (12 mM), $MgCl_2$ (2 mM), ATP (1 mM), DTT (1 mM), BSA (0.1 mg/ml), NADH (0.5 mM), PEP (1.5 mM), pyruvate kinase (4 U/ml), lactate dehydrogenase (8 U/ml), and antifoam (90 ppm). The pH is adjusted to 6.80 at 22° C. by addition of potassium hydroxide. Calcium levels are controlled by a buffering system containing 0.6 mM EGTA and varying concentrations of calcium, to achieve a free calcium concentration of $1 \times 10^{-4}$ M to $1 \times 10^{-8}$ M.

The protein components specific to this assay are bovine cardiac myosin subfragment-1 (typically 0.5 μM), bovine cardiac actin (14 μM), bovine cardiac tropomyosin (typically 3 μM), and bovine cardiac troponin (typically 3-8 μM). The exact concentrations of tropomyosin and troponin are determined empirically, by titration to achieve maximal difference in ATPase activity when measured in the presence of 1 mM EGTA versus that measured in the presence of 0.2 mM $CaCl_2$. The exact concentration of myosin in the assay is also determined empirically, by titration to achieve a desired rate of ATP hydrolysis. This varies between protein preparations, due to variations in the fraction of active molecules in each preparation.

Compound dose responses are typically measured at the calcium concentration corresponding to 50% of maximal ATPase activity ($pCa_{50}$), so a preliminary experiment is performed to test the response of the ATPase activity to free calcium concentrations in the range of $1 \times 10^{-4}$ M to $1 \times 10^{-8}$ M. Subsequently, the assay mixture is adjusted to the $pCa_{50}$ (typically $3 \times 10^{-7}$ M). Assays are performed by first preparing a dilution series of test compound, each with an assay mixture containing potassium PIPES, $MgCl_2$, BSA, DTT, pyruvate kinase, lactate dehydrogenase, myosin subfragment-1, antifoam, EGTA, $CaCl_2$, and water. The assay is started by adding an equal volume of solution containing potassium Pipes, MgCl$_2$, BSA, DTT, ATP, NADH, PEP, actin, tropomyosin, troponin, antifoam, and water. ATP hydrolysis is monitored by absorbance at 340 nm. The resulting dose response curve is fit by the 4 parameter equation y=Bottom+((Top−Bottom)/(1+((EC50/X)^Hill))). The AC1.4 is defined as the concentration at which ATPase activity is 1.4-fold higher than the bottom of the dose curve.

Example 5

Myocyte Assays

A. PREPARATION OF ADULT CARDIAC VENTRICULAR RAT MYOCYTES. Adult male Sprague-Dawley rats are anesthetized with a mixture of isoflurane gas and oxygen. Hearts are quickly excised, rinsed and the ascending aorta cannulated. Continuous retrograde perfusion is initiated on the hearts at a perfusion pressure of 60 cm H$_2$O. Hearts are first perfused with a nominally Ca$^{2+}$ free modified Krebs solution of the following composition: 110 mM NaCl, 2.6 mM KCl, 1.2 mM KH$_2$PO$_4$ 7H$_2$O, 1.2 mM MgSO$_4$, 2.1 mM NaHCO$_3$, 11 mM glucose and 4 mM Hepes (all Sigma). This medium is not recirculated and is continually gassed with O$_2$. After approximately 3 minutes the heart is perfused with modified Krebs buffer supplemented with 3.3% collagenase (169µ/mg activity, Class II, Worthington Biochemical Corp., Freehold, N.J.) and 25 µM final calcium concentration until the heart becomes sufficiently blanched and soft. The heart is removed from the cannulae, the atria and vessels discarded and the ventricles are cut into small pieces. The myocytes are dispersed by gentle agitation of the ventricular tissue in fresh collagenase containing Krebs prior to being gently forced through a 200 µm nylon mesh in a 50 cc tube. The resulting myocytes are resuspended in modified Krebs solution containing 25 µm calcium. Myocytes are made calcium tolerant by addition of a calcium solution (100 mM stock) at 10 minute intervals until 100 µM calcium is achieved. After 30 minutes the supernatant is discarded and 30-50 ml of Tyrode buffer (137 mM NaCl, 3.7 mM KCl, 0.5 mM MgCl, 11 mM glucose, 4 mM Hepes, and 1.2 mM CaCl$_2$, pH 7.4) is added to cells. Cells are kept for 60 min at 37° C. prior to initiating experiments and used within 5 hrs of isolation. Preparations of cells are used only if cells first passed QC criteria by responding to a standard (>150% of basal) and isoproterenol (ISO; >250% of basal). Additionally, only cells whose basal contractility is between 3 and 8% are used in the following experiments.

B. ADULT VENTRICULAR MYOCYTE CONTRACTILITY EXPERIMENTS. Aliquots of Tyrode buffer containing myocytes are placed in perfusion chambers (series 20 RC-27NE; Warner Instruments) complete with heating platforms. Myocytes are allowed to attach, the chambers heated to 37° C., and the cells then perfused with 37° C. Tyrode buffer. Myocytes are field stimulated at 1 Hz in with platinum electrodes (20% above threshold). Only cells that have clear striations, and are quiescent prior to pacing are used for contractility experiments. To determine basal contractility, myocytes are imaged through a 40× objective and using a variable frame rate (60-240 Hz) charge-coupled device camera, the images are digitized and displayed on a computer screen at a sampling speed of 240 Hz. [Frame grabber, myopacer, acquisition, and analysis software for cell contractility are available from IonOptix (Milton, Mass.).] After a minimum 5 minute basal contractility period, test compounds (0.01-15 µM) are perfused on the myocytes for 5 minutes. After this time, fresh Tyrode buffer is perfused to determine compound washout characteristics. Using edge detection strategy, contractility of the myocytes and contraction and relaxation velocities are continuously recorded.

C. CONTRACTILITY ANALYSIS: Three or more individual myocytes are tested per compound, using two or more different myocyte preparations. For each cell, twenty or more contractility transients at basal (defined as 1 min prior to compound infusion) and after compound addition, are averaged and compared. These average transients are analyzed to determine changes in diastolic length, and using the Ionwizard analysis program (IonOptix), fractional shortening (% decrease in the diastolic length), and maximum contraction and relaxation velocities (um/sec) are determined. Analysis of individual cells are combined. Increase in fractional shortening over basal indicates potentiation of myocyte contractility.

D. CALCIUM TRANSIENT ANALYSIS: Fura loading: Cell permeable Fura-2 (Molecular Probes) is dissolved in equal amounts of pluronic (Mol Probes) and FBS for 10 min at RT. A 1 µM Fura stock solution is made in Tyrode buffer containing 500 mM probenecid (Sigma). To load cells, this solution is added to myocytes at RT. After 10 min. the buffer is removed, the cells washed with Tyrode containing probenecid and incubated at RT for 10 min. This wash and incubation is repeated. Simultaneous contractility and calcium measurements are determined within 40 min. of loading.

Imaging: A test compound is perfused on cells. Simultaneous contractility and calcium transient ratios are determined at baseline and after compound addition. Cells are digitally imaged and contractility determined as described above, using that a red filter in the light path to avoid interference with fluorescent calcium measurements. Acquisition, analysis software and hardware for calcium transient analysis are obtained from IonOptix. The instrumentation for fluorescence measurement includes a xenon arc lamp and a Hyperswitch dual excitation light source that alternates between 340 and 380 wavelengths at 100 Hz by a galvo-driven mirror. A liquid filled light guide delivers the dual excitation light to the microscope and the emission fluorescence is determined using a photomultiplier tube (PMT). The fluorescence system interface routes the PMT signal and the ratios are recorded using the IonWizard acquisition program.

Analysis: For each cell, ten or more contractility and calcium ratio transients at basal and after compound addition, where averaged and compared. Contractility average transients are analyzed using the Ionwizard analysis program to determine changes in diastolic length, and fractional shortening (% decrease in the diastolic length). The averaged calcium ratio transients are analyzed using the Ionwizard analysis program to determine changes in diastolic and systolic ratios and the 75% time to baseline ($T_{75}$).

E. DURABILITY: To determine the durability of response, myocytes are challenged with a test compound for 25 minutes followed by a 2 min. washout period. Contractility response is compared at 5 and 25 min. following compound infusion.

F. THRESHOLD POTENTIAL: Myocytes are field stimulated at a voltage approximately 20% above threshold. In these experiments the threshold voltage (minimum voltage to pace cell) is empirically determined, the cell paced at that threshold and then the test compound is infused. After the compound activity is at steady state, the voltage is decreased for 20 seconds and then restarted. Alteration of ion channels corresponds to increasing or lowering the threshold action potential.

G. Hz FREQUENCY: Contractility of myocytes is determined at 3 Hz as follows: a 1 min. basal time point followed by perfusion of the test compound for 5 min. followed by a 2 min. washout. After the cell contractility has returned completely to baseline the Hz frequency is decreased to 1. After an initial acclimation period the cell is challenged by the same compound. As this species, rat, exhibits a negative force frequency at 1 Hz, at 3 Hz the FS of the cell should be lower, but the cell should still respond by increasing its fractional shortening in the presence of the compound.

H. ADDITIVE WITH ISOPROTERENOL: To demonstrate that a compound act via a different mechanism than the adrenergic stimulant isoproterenol, cells are loaded with fura-2 and simultaneous measurement of contractility and calcium ratios are determined. The myocytes are sequentially challenged with 5 µm a test compound, buffer, 2 nM isoproterenol, buffer, and a combination of a test compound and isoproterenol.

Example 6

In Vitro Model of Dose Dependent Cardiac Myosin ATPase Modulation

Bovine and rat cardiac myosins are purified from the respective cardiac tissues. Skeletal and smooth muscle myosins used in the specificity studies are purified from rabbit skeletal muscle and chicken gizzards, respectively. All myosins used in the assays are converted to a single-headed soluble form (S1) by a limited proteolysis with chymotrypsin. Other sarcomeric components: troponin complex, tropomyosin and actin are purified from bovine hearts (cardiac sarcomere) or chicken pectoral muscle (skeletal sarcomere).

Activity of myosins is monitored by measuring the rates of hydrolysis of ATP. Myosin ATPase is very significantly activated by actin filaments. ATP turnover is detected in a coupled enzymatic assay using pyruvate kinase (PK) and lactate dehydrogenase (LDH). In this assay each ADP produced as a result of ATP hydrolysis is recycled to ATP by PK with a simultaneous oxidation of NADH molecule by LDH. NADH oxidation can be conveniently monitored by decrease in absorbance at 340 nm wavelength.

Dose responses are measured using a calcium-buffered, pyruvate kinase and lactate dehydrogenase-coupled ATPase assay containing the following reagents (concentrations expressed are final assay concentrations): Potassium PIPES (12 mM), $MgCl_2$ (2 mM), ATP (1 mM), DTT (1 mM), BSA (0.1 mg/ml), NADH (0.5 mM), PEP (1.5 mM), pyruvate kinase (4 U/ml), lactate dehydrogenase (8 U/ml), and antifoam (90 ppm). The pH is adjusted to 6.80 at 22° C. by addition of potassium hydroxide. Calcium levels are controlled by a buffering system containing 0.6 mM EGTA and varying concentrations of calcium, to achieve a free calcium concentration of $1 \times 10^{-4}$ M to $1 \times 10^{-8}$ M.

The protein components specific to this assay are bovine cardiac myosin subfragment-1 (typically 0.5 µM), bovine cardiac actin (14 µM), bovine cardiac tropomyosin (typically 3 µM), and bovine cardiac troponin (typically 3-8 µM). The exact concentrations of tropomyosin and troponin are determined empirically, by titration to achieve maximal difference in ATPase activity when measured in the presence of 1 mM EGTA versus that measured in the presence of 0.2 mM $CaCl_2$. The exact concentration of myosin in the assay is also determined empirically, by titration to achieve a desired rate of ATP hydrolysis. This varies between protein preparations, due to variations in the fraction of active molecules in each preparation.

Compound dose responses are typically measured at the calcium concentration corresponding to 50% of maximal ATPase activity ($pCa_{50}$), so a preliminary experiment is performed to test the response of the ATPase activity to free calcium concentrations in the range of $1 \times 10^{-4}$ M to $1 \times 10^{-8}$ M. Subsequently, the assay mixture is adjusted to the $pCa_{50}$ (typically $3 \times 10^{-7}$ M). Assays are performed by first preparing a dilution series of test compound, each with an assay mixture containing potassium Pipes, $MgCl_2$, BSA, DTT, pyruvate kinase, lactate dehydrogenase, myosin subfragment-1, antifoam, EGTA, $CaCl_2$, and water. The assay is started by adding an equal volume of solution containing potassium Pipes, $MgCl_2$, BSA, DTT, ATP, NADH, PEP, actin, tropomyosin, troponin, antifoam, and water. ATP hydrolysis is monitored by absorbance at 340 nm. The resulting dose response curve is fit by the 4 parameter equation y=Bottom+((Top−Bottom)/(1+((EC50/X)^Hill))). The AC1.4 is defined as the concentration at which ATPase activity is 1.4-fold higher than the bottom of the dose curve.

Ability of a compound to activate cardiac myosin is evaluated by the effect of the compound on the actin stimulated ATPase of S1 subfragment. Actin filaments in the assay are decorated with troponin and tropomyosin and Ca++ concentration is adjusted to a value that would result in 50% of maximal activation. S1 ATPase is measured in the presence of a dilution series of the compound. Compound concentration required for 40% activation above the ATPase rate measured in the presence of control (equivalent volume of DMSO) is reported as $AC_{40}$.

Example 7

In Vivo Fractional Shortening Assay

A. ANIMALS Male Sprague Dawley rats from Charles River Laboratories (275-350 g) are used for bolus efficacy and infusion studies. Heart failure animals are described below. They are housed two per cage and have access to food and water ad libitum. There is a minimum three-day acclimation period prior to experiments.

B. ECHOCARDIOGRAPHY Animals are anesthetized with isoflurane and maintained within a surgical plane throughout the procedure. Core body temperature is maintained at 37° C. by using a heating pad. Once anesthetized, animals are shaven and hair remover is applied to remove all traces of fur from the chest area. The chest area is further prepped with 70% ETOH and ultrasound gel is applied. Using a GE System Vingmed ultrasound system (General Electric Medical Systems), a 10 MHz probe is placed on the chest wall and images are acquired in the short axis view at the level of the papillary muscles. 2-D M-mode images of the left ventricle are taken prior to, and after, compound bolus injection or infusion. In vivo fractional shortening ((end diastolic diameter−end systolic diameter)/end diastolic diameter×100) is determined by analysis of the M-mode images using the GE EchoPak software program.

C. BOLUS AND INFUSION EFFICACY For bolus and infusion protocols, fractional shortening is determined using echocardiography as described above. For bolus and infusion protocols, five pre-dose M-Mode images are taken at 30 second intervals prior to bolus injection or infusion of compounds. After injection, M-mode images are taken at 1 min and at five minute intervals thereafter up to 30 min. Bolus injection (0.5-5 mg/kg) or infusion is via a tail vein catheter. Infusion parameters are determined from pharmacokinetic profiles of the compounds. For infusion, animals received a 1 minute loading dose immediately followed by a 29 minute infusion dose via a tail vein catheter. The loading dose is calculated by determining the target concentration×the steady state volume of distribution. The maintenance dose concentration is determined by taking the target concentration×the clearance. Compounds are formulated in 25% cavitron vehicle for bolus and infusion protocols. Blood samples are taken to determine the plasma concentration of the compounds.

Example 8

Hemodynamics in Normal and Heart Failure Animals

Animals are anesthetized with isoflurane, maintained within a surgical plane, and then shaven in preparation for catheterization. An incision is made in the neck region and the right carotid artery cleared and isolated. A 2 French Millar Micro-tip Pressure Catheter (Millar Instruments, Houston, Tex.) is cannulated into the right carotid artery and threaded past the aorta and into the left ventricle. End diastolic pressure readings, max+/− dp/dt, systolic pressures and heart rate are determined continuously while compound or vehicle is infused. Measurements are recorded and analyzed using a PowerLab and the Chart 4 software program (ADInstruments, Mountain View, Calif.). Hemodynamics measurements are performed at a select infusion concentration. Blood samples are taken to determine the plasma concentration of the compounds.

Example 9

Left Coronary Artery Occlusion Model of Congestive Heart Failure

A. ANIMALS Male Sprague-Dawley CD (220-225 g; Charles River) rats are used in this experiment. Animals are allowed free access to water and commercial rodent diet under standard laboratory conditions. Room temperature is maintained at 20-23° C. and room illumination is on a 12/12-hour light/dark cycle. Animals are acclimatized to the laboratory environment 5 to 7 days prior to the study. The animals are fasted overnight prior to surgery.

B. OCCLUSION PROCEDURE Animals are anaesthetized with ketamine/xylazine (95 mg/kg and 5 mg/kg) and intubated with a 14-16-gauge modified intravenous catheter. Anesthesia level is checked by toe pinch. Core body temperature is maintained at 37° C. by using a heating blanket. The surgical area is clipped and scrubbed. The animal is placed in right lateral recumbency and initially placed on a ventilator with a peak inspiratory pressure of 10-15 cm $H_2O$ and respiratory rate 60-110 breaths/min. 100% $O_2$ is delivered to the animals by the ventilator. The surgical site is scrubbed with surgical scrub and alcohol. An incision is made over the rib cage at the $4^{th}$-$5^{th}$ intercostal space. The underlying muscles are dissected with care to avoid the lateral thoracic vein, to expose the intercostal muscles. The chest cavity is entered through $4^{th}$-$5^{th}$ intercostal space, and the incision expanded to allow visualization of the heart. The pericardium is opened to expose the heart. A 6-0 silk suture with a taper needle is passed around the left coronary artery near its origin, which lies in contact with the left margin of the pulmonary cone, at about 1 mm from the insertion of the left auricular appendage. The left coronary artery is occluded by tying the suture around the artery ("LCO"). Sham animals are treated the same, except that the suture is not tied. The incision is closed in three layers. The rat is ventilated until able to ventilate on its own. The rats are extubated and allowed to recover on a heating pad. Animals receive buprenorphine (0.01-0.05 mg/kg SQ) for post operative analgesia. Once awake, they are returned to their cage. Animals are monitored daily for signs of infection or distress. Infected or moribund animals are euthanized. Animals are weighed once a week.

C. EFFICACY ANALYSIS Approximately eight weeks after infarction surgery, rats are scanned for signs of myocardial infarction using echocardiography. Only those animals with decreased fractional shortening compared to sham rats are utilized further in efficacy experiments. In all experiments, there are four groups, sham+vehicle, sham+compound, LCL+vehicle and LCL+compound. At 10-12 weeks post LCL, rats are infused at a select infusion concentration. As before, five pre-dose M-Mode images are taken at 30 second intervals prior to infusion of compounds and M-mode images are taken at 30 second intervals up to 10 minutes and every minute or at five minute intervals thereafter. Fractional shortening is determined from the M-mode images. Comparisons between the pre-dose fractional shortening and compound treatment are performed by ANOVA and a post-hoc Student-Newman-Keuls. Animals are allowed to recover and within 7-10 days, animals are again infused with compounds using the hemodynamic protocol to determine hemodynamic changes of the compounds in heart failure animals. At the end to the infusion, rats are killed and the heart weights determined.

When tested as described in Examples above, compounds of Formula I are shown to have the desired activity.

Example 10

Pharmaceutical Composition

A pharmaceutical composition for intravenous administration is prepared in the following manner.

1 mg/mL (as free base) IV solution with the vehicle being 50 mM citric acid, pH adjusted to 5.0 with NaOH:

| Composition | Unit Formula (mg/mL) |
| --- | --- |
| Active Agent | 1.00 |
| Citric Acid | 10.51 |
| Sodium Hydroxide | qs to pH 5.0 |
| Water for Injection (WFI) | q.s. to 1 mL |

*All components other than the active compound are USP/Ph. Eur. compliant

A suitable compounding vessel is filled with WFI to approximately 5% of the bulk solution volume. The citric acid (10.51 g) is weighed, added to the compounding vessel and stirred to produce 1 M citric acid. The active agent (1.00 g) is weighed and dissolved in the 1 M citric acid solution. The resulting solution is transferred to a larger suitable compounding vessel and WFI is added to approximately 85% of the bulk solution volume. The pH of the bulk solution is measured and adjusted to 5.0 with 1 N NaOH. The solution is brought to its final volume (1 liter) with WFI.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. At least one chemical entity chosen from compounds of Formula I

[Formula I structure]

and pharmaceutically acceptable salts, wherein

T is —O—;

W, X, Y, and Z are —C═;

$R_1$ is optionally substituted alkyl;

$R_2$ is optionally substituted pyridin-3-yl;

$R_3$ is hydrogen;

$R_4$ is fluoro; and $R_5$ is hydrogen;

$R_6$ and $R_7$ are hydrogen; and $R_{13}$ is hydrogen.

2. At least one chemical entity of claim 1 wherein $R_1$ is substituted lower alkyl optionally substituted with one or two groups chosen from optionally substituted alkoxy and optionally substituted amino.

3. At least one chemical entity of claim 1 where $R_1$ is selected from 1-methoxypropan-2-yl, (1-acetamidocyclopentyl)methyl, 2-acetamido-2-methylprop-1-yl, 2-(methoxycarbonylamino)eth-1-yl, 2-(tert-butoxycarbonyl(methyl)amino)eth-1-yl, 1-(methoxycarbonyl(methyl)amino)propan-2-yl, 1-(tert-butoxycarbonyl(methyl)amino)propan-2-yl, 2-acetamidoeth-1-yl, 2-(N-methylacetamido)eth-1-yl, 1-(N-methylacetamido)propan-2-yl, 2-(N,N-dimethylsulfamoylamino)eth-1-yl, 2-((N,N-dimethylsulfamoyl)(methyl)amino)eth-1-yl, 1-((N,N-dimethylsulfamoyl)(methyl)amino)propan-2-yl, 2-(ethylsulfonamido)eth-1-yl, 2-(N-methylethylsulfonamido)eth-1-yl, 1-(N-methylethylsulfonamido)propan-2-yl, 1-(N-methylpropan-2-ylsulfonamido)propan-2-yl, 2-(N-methylpropan-2-ylsulfonamido)eth-1-yl, 2-(2-cyano-1,3,3-trimethylguanidino)eth-1-yl, 2-(methylamino)eth-1-yl, 5-methyl-1,1-dioxo-1$\lambda^6$-[1,2,5]thiadiazolidin-2-yl-ethyl; 5-methyl-1,1-dioxo-1$\lambda^6$-[1,2,5]thiadiazolidin-3-yl-methyl; 2,6-dimethyl-1,1-dioxo-1$\lambda^6$-[1,2,6]thiadiazinan-4-yl-methyl,

[structures]

4. At least one chemical entity of claim 3 where $R_1$ is selected from 2-(methoxycarbonylamino)eth-1-yl, 1-(methoxycarbonyl(methyl)amino)propan-2-yl, 2-acetamido-2-methylprop-1-yl, 2-(N,N-dimethylsulfamoylamino)eth-1-yl, 2-((N,N-dimethylsulfamoyl)(methyl)amino)eth-1-yl, 1-((N,N-dimethylsulfamoyl)(methyl)amino)propan-2-yl, 2-(ethylsulfonamido)eth-1-yl, 2-(N-methylethylsulfonamido)eth-1-yl, 1-(N-methylethylsulfonamido)propan-2-yl, 1-(N-methylpropan-2-ylsulfonamido)propan-2-yl, and 2-(N-methylpropan-2-ylsulfonamido)eth-1-yl.

5. At least one chemical entity of claim 1 wherein $R_2$ is pyridin-3-yl optionally substituted with lower alkyl.

6. At least one chemical entity of claim 1 wherein the compound of Formula I is chosen from N-[5-fluoro-3-(2-methoxy-isopropoxy)phenyl][(6-methoxy(3-pyridyl))amino]carboxamide;

N-[5-fluoro-3-(2-methoxy-isopropoxy)phenyl](3-pyridylamino)carboxamide;

[(6-methoxy(3-pyridyl))amino]-N-[3-(methylethoxy)phenyl]carboxamide;

N-[({5-fluoro-3-[(N-(3-pyridyl)carbamoyl)amino]phenoxy}methyl)cyclopentyl]acetamide;

N-(2-{5-fluoro-3-[(N-(3-pyridyl)carbamoyl)amino]phenoxy}-tert-butyl)acetamide;

N-{2-[5-fluoro-3-({N-[6-(trifluoromethyl)(3-pyridyl)]carbamoyl}amino)phenoxy]-tert-butyl}acetamide;

N-[2-(5-fluoro-3-{[N-(6-methoxy(3-pyridyl))carbamoyl]amino}phenoxy)-tert-butyl]acetamide;

N-({[3-fluoro-5-({[6-(trifluoromethyl)(3-pyridyl)]amino}carbonylamino)phenoxy]methyl}cyclopentyl)acetamide;

N-{[(3-fluoro-5-{[(6-methoxy(3-pyridyl))amino]carbonylamino}phenoxy)methyl]cyclopentyl}acetamide;

N-{5-fluoro-3-[2-(methoxycarbonylamino)ethoxy]phenyl}(3-pyridylamino)carboxamide;

N-(2-{3-fluoro-5-[(3-pyridylamino)carbonylamino]phenoxy}ethyl)acetamide;

N-[3-(2-{[(dimethylamino)sulfonyl]amino}ethoxy)-5-fluorophenyl](3-pyridylamino)carboxamide;

N-(3-{2-[(ethylsulfonyl)amino]ethoxy}-5-fluorophenyl)(3-pyridylamino)carboxamide;

N-(2-{3-fluoro-5-[(3-pyridylamino)carbonylamino]phenoxy}ethyl)methoxy-N-methylcarboxamide;

N-(2-{3-fluoro-5-[(3-pyridylamino)carbonylamino]phenoxy}ethyl)-N-methylacetamide;

N-[3-(2-{[(dimethylamino)sulfonyl]methylamino}ethoxy)-5-fluorophenyl](3-pyridylamino)carboxamide;

N-(3-{2-[(ethylsulfonyl)methylamino]ethoxy}-5-fluorophenyl)(3-pyridylamino)carboxamide;

N-[3-(2-{[(1Z)-1-(dimethylamino)-2-cyano-2-azavinyl]methylamino}ethoxy)-5-fluorophenyl](3-pyridylamino)carboxamide;

N-[3-((1R)-2-{[dimethylamino)sulfonyl]methylamino}-isopropoxy)-5-fluorophenyl](3-pyridylamino)carboxamide;

N-(3-{(1R)-2-[(ethylsulfonyl)methylamino]-isopropoxy}-5-fluorophenyl)(3-pyridylamino)carboxamide;

N-(3-{(1R)-2-[(tert-butoxy)-N-methylcarbonylamino]-isopropoxy}-5-fluorophenyl)(3-pyridylamino)carboxamide;

N-{3-[(1R)-2-(methoxy-N-methylcarbonylamino)-isopropoxy]-5-fluorophenyl}(3-pyridylamino)carboxamide;

N-{3-[(1R)-1-methyl-2-(methylamino)ethoxy]-5-fluorophenyl}(3-pyridylamino)carboxamide;

N-[3-((1S)-2-{[dimethylamino)sulfonyl]methylamino}-isopropoxy)-5-fluorophenyl]-3-pyridylamino)carboxamide;

N-(3-{(1S)-2-[(ethylsulfonyl)methylamino]-isopropoxy}-5-fluorophenyl)(3-pyridylamino)carboxamide;

N-((2S)-2-{3-fluoro-5-[(3-pyridylamino)carbonylamino]phenoxy}propyl)methoxy-N-methylcarboxamide;

N-((2S)-2-{3-fluoro-5-[(3-pyridylamino)carbonylamino]phenoxy}propyl)-N-methylacetamide;

N-[3-(2-{[(1E)-1-(dimethylamino)-2-cyano-2-azavinyl]methylamino}(1S)-isopropoxy)-5-fluorophenyl](3-pyridylamino)carboxamide;

N-[3-((1S)-1-methyl-2-{methyl[(methylethyl)sulfonyl]amino}ethoxy)-5-fluorophenyl](3-pyridylamino)carboxamide;

N-((2R)-2-{3-fluoro-5-[(3-pyridylamino)carbonylamino]phenoxy}propyl)-N-methylacetamide;

N-[3-(2-{[(1E)-1-(dimethylamino)-2-cyano-2-azavinyl]methylamino}(1R)-isopropoxy)-5-fluorophenyl](3-pyridylamino)carboxamide;

N-[3-(2-{[(dimethylamino)sulfonyl]methylamino}ethoxy)-5-fluorophenyl][(6-methyl(3-pyridyl))amino]carboxamide;

N-(3-{2-[(ethylsulfonyl)methylamino]ethoxy}-5-fluorophenyl)[(6-methyl(3-pyridyl))amino]carboxamide;

N-[5-fluoro-3-(2-{methyl[(methylethyl)sulfonyl]amino}ethoxy)phenyl][(6-methyl(3-pyridyl))amino]carboxamide;

N-[3-(2-{[(dimethylamino)sulfonyl]methylamino}ethoxy)-5-fluorophenyl][(4-fluorophenyl)amino]carboxamide;

N-(3-{2-[(ethylsulfonyl)methylamino]ethoxy}-5-fluorophenyl)[(4-fluorophenyl)amino]carboxamide;

N-[5-fluoro-3-(2-{methyl[(methylethyl)sulfonyl]amino}ethoxy)phenyl][(4-fluorophenyl)amino]carboxamide;

N-(3-{(1R)-2-[(tert-butoxy)-N-methylcarbonylamino]-isopropoxy}-5-fluorophenyl)[(6-methyl(3-pyridyl))amino]carboxamide;

N-[3-((1R)-2-{[(dimethylamino)sulfonyl]methylamino}-isopropoxy)-5-fluorophenyl][(6-methyl(3-pyridyl))amino]carboxamide;

N-(3-{(1R)-2-[(ethylsulfonyl)methylamino]-isopropoxy}-5-fluorophenyl)[(6-methyl(3-pyridyl))amino]carboxamide;

N-[3-((1R)-1-methyl-2-{methyl[(methylethyl)sulfonyl]amino}ethoxy)-5-fluorophenyl][(6-methyl(3-pyridyl))amino]carboxamide;

N-{3-[(1R)-2-(methoxy-N-methylcarbonylamino)-isopropoxy]-5-fluorophenyl}[(6-methyl(3-pyridyl))amino]carboxamide;

N-[3-((1S)-2-{[(dimethylamino)sulfonyl]methylamino}-isopropoxy)-5-fluorophenyl][(6-methyl(3-pyridyl))amino]carboxamide;

N-(3-{(1S)-2-[(ethylsulfonyl)methylamino]-isopropoxy}-5-fluorophenyl)[(6-methyl(3-pyridyl))amino]carboxamide;

N-[3-((1S)-1-methyl-2-{methyl[(methylethyl)sulfonyl]amino}ethoxy)-5-fluorophenyl][(6-methyl(3-pyridyl))amino]carboxamide;

N-[(2S)-2-(3-fluoro-5-{[(6-methyl(3-pyridyl))amino]carbonylamino}phenoxy)propyl]methoxy-N-methylcarboxamide;

N-[(2S)-2-(3-fluoro-5-{[(6-methyl(3-pyridyl))amino]carbonylamino}phenoxy)propyl]-N-methylacetamide;

N-[3-(2-{[(1E)-1-(dimethylamino)-2-cyano-2-azavinyl]methylamino}(1S)-isopropoxy)-5-fluorophenyl][(6-methyl(3-pyridyl))amino]carboxamide;

N-{3-[2-{[(dimethylamino)sulfonyl]methylamino}-1-({[(dimethylamino)sulfonyl]methylamino}methyl)ethoxy]-5-fluorophenyl}(3-pyridylamino)carboxamide;

N-{3-[2-{[(dimethylamino)sulfonyl]methylamino}-1-({[(dimethylamino)sulfonyl]methylamino}methyl)ethoxy]-5-fluorophenyl}[(6-methyl(3-pyridyl))amino]carboxamide;

N-{5-fluoro-3-[2-(5-methyl-1,1-dioxo(1,2,5-thiadiazolidin-2-yl))ethoxy]phenyl}(3-pyridylamino)carboxamide;

N-{5-fluoro-3-[2-(5-methyl-1,1-dioxo(1,2,5-thiadiazolidin-2-yl))ethoxy]phenyl}[(6-methyl(3-pyridyl))amino]carboxamide;

N-{3-[(2,5-dimethyl-1,1-dioxo(1,2,5-thiadiazolidin-3-yl))methoxy]-5-fluorophenyl}(3-pyridylamino)carboxamide; and N-{3-[(2,5-dimethyl-1,1-dioxo(1,2,5-thiadiazolidin-3-yl))methoxy]-5-fluorophenyl}[(6-methyl(3-pyridyl))amino]carboxamide.

7. A pharmaceutical composition comprising a pharmaceutically acceptable excipient or adjuvant and at least one chemical entity of claim 1.

8. The pharmaceutical composition of claim 7 wherein the composition is formulated in a form chosen from injectable fluids, aerosols, tablets, pills, capsules, syrups, creams, gels, and transdermal patches.

* * * * *